United States Patent [19]

Nofre et al.

[11] Patent Number: 4,921,939

[45] Date of Patent: May 1, 1990

[54] SWEETENING AGENTS

[75] Inventors: Claude Nofre, Lyon; Jean M. Tinti, Meyzieu; Farroudja Ouar Chatzopoulos, Saint Etienne, all of France

[73] Assignee: Universite Claude Bernard -Lyon 1, France

[21] Appl. No.: 21,359

[22] Filed: Mar. 3, 1987

Related U.S. Application Data

[63] Continuation-in-part of Ser. No. 836,071, Mar. 4, 1986, Pat. No. 4,877,895.

[30] Foreign Application Priority Data

| Mar. 19, 1985 | [FR] | France | 85 04242 |
| Mar. 13, 1986 | [EP] | European Pat. Off. | 86420071 |
| Apr. 10, 1986 | [FR] | France | 86 05320 |
| Nov. 7, 1986 | [FR] | France | 86 15788 |
| Dec. 23, 1986 | [FR] | France | 86 18233 |

[51] Int. Cl.$^5$ .................. C07C 127/19; C07C 129/12; A23L 1/236; A23L 1/18

[52] U.S. Cl. ............................. 558/414; 558/418; 562/430; 562/434; 562/440; 426/548; 514/426

[58] Field of Search ............... 562/440, 439, 430, 434; 560/22, 251, 21; 558/414, 413, 418

[56] References Cited

U.S. PATENT DOCUMENTS

| 3,492,131 | 1/1970 | Schlatter | 99/141 |
| 3,642,491 | 2/1972 | Schlatter | 99/28 |
| 3,714,139 | 1/1973 | Schlatter | 260/112.5 |
| 3,800,046 | 3/1974 | Schlatter | 426/168 |
| 4,426,521 | 1/1984 | Tanaka et al. | 544/146 |
| 4,656,678 | 2/1987 | Nofre et al. | 426/548 |
| 4,673,582 | 6/1987 | Nofre et al. | 426/548 |

FOREIGN PATENT DOCUMENTS

| 1027113 | 2/1978 | Canada . |
| 0048051 | 3/1982 | European Pat. Off. . |
| 0241395 | 12/1987 | European Pat. Off. . |
| 2533210 | 9/1982 | France . |

OTHER PUBLICATIONS

Journal of Agricultural and Food Chemistry, vol. 28, No. 6, 1980, pp. 1338–1340.

Chemische Berichte, vol. 94, No. 7, 1961, pp. 1814–1824, Weinheim, DE; F. Micheel et al., with translation.

Y. Ariyoshi et al., The Structure-Taste Relationships of the Dipeptide Esters Composed of L-Aspartic Acid and B-Hydroxy Amino Acids, Bulletin of the Chemical Society of Japan, 02/1974, pp. 326–330.

Tinti, J. M. et al., Studies on Sweetners Requiring the Simultaneous Presence of Both the $NO_2$/CN and COO-Groups, Naturwissenschaften 68, Dec. 1981, pp. 143–145.

Tinti, J. M. et al., Sweet Taste Receptor, Naturwissenschaften 67, Jan. 2, 1980, pp. 193–194.

Miller et al., A. Facile Conversion of Amino Acids to Guanidinio Acids, Communications, Sep. 1986, pp. 777–779.

*Primary Examiner*—Anton H. Sutto
*Attorney, Agent, or Firm*—Arnold, White & Durkee

[57] ABSTRACT

Substituted guanidines and ethanamidines are provided as high potency sweetening agents.

37 Claims, No Drawings

SWEETENING AGENTS

This application is a continuation-in-part of U.S. patent application Ser. No. 836,071 filed Mar. 4, 1986, now U.S. Pat. No. 4,877,895.

BACKGROUND

The present invention relates to new sweetening agents for sweetening food, drinks, confectionery, chewing gums, hygiene products, cosmetics, pharmaceutical and veterinary products, and the like. It also relates to the products and compositions containing such sweetening agents.

Among the chemical compounds presenting sweetening properties, "suosan" and its derivatives constitute a chemical series which has been widely studied since its discovery in 1948 by Petersen and Muller (See, for example, Beets, pp. 336–337, in "Structure-Activity Relationships in Human Chemoreception", Applied Science Publ., London, 1978; Crosby and Wingard, p. 160, in "Developments in Sweeteners", Applied Science Publ., London, 1979; Tinti, Nofre and Peytavi, Z. Lebensm. Unters. Forsch., 175, 266–268, 1982). These compounds have not been put to commercial use as sweeteners because: (1) certain of them release potentially toxic molecules ("suosan", for example, can give rise to p-nitroaniline); (2) certain of them contain ureido or thioureido groups which undergo slow hydrolysis in aqueous solution; and (3) certain others, apart from their sweet taste, generate undesirable liquorice or bitter aftertastes.

Of further interest to the present invention is the disclosure of Yuki and Inoue (Nippon Kagaku Kaishi, no. 11, 2140–43 (1974)), Chemical Abstracts, Vol. 82, no. 140061p (1975) which describes N-((4-chlorophenylamino)iminomethyl)-β-alanine (Chemical Substance Index, vol. 76–85, 1972–1976, p. 1067cs). This compound fails to present the high potency sweetening properties of the compounds of the present invention.

Also of interest to the present invention are the disclosures of the inventors in their own European patent application No. 0,107,597 published May 2, 1984 (U.S. Pat. No. 4,645,678) and European patent application No. 0,195,731 published Sept. 24, 1986 corresponding to French patent application No. 85.04241. These applications disclose suosan derivatives characterized by the replacement of the beta-alanine group present in the suosan molecule with sweet dipeptide ester moieties such as aspartame (L-aspartyl-L-phenylalanine methyl ester). The sweet suosan/dipeptide derivatives disclosed by the above two patent applications are also characterized by replacement of the oxygen defining the urea structure by sulfur to form a thiourea, by a nitrogen to form a guanidine or by a carbon to form an amidine structure. Such compounds, while disclosed as having sweetness potencies as high as 55,000 times that of a 2% sucrose solution on a by weight basis, suffer from limitations relating to solubility and/or instability in the presence of elevated temperatures. The sweetening potency of aspartame, by comparison, is about 180 times that of a 2% sucrose solution on a by weight basis.

BRIEF SUMMARY

According to the present invention, substituted guanidino and ethanamidino sweetening agents are provided which correspond to the general formula:

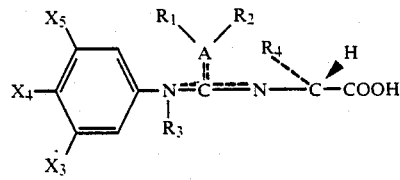

wherein $X_3$, $X_4$ and $X_5$ are the same or different and are selected from the group consisting of
H,
Br,
$CF_3$,
$CF_2CF_3$,
$CH_2CF_3$,
$C_1$–$C_4$ alkyl,
$CH=NOCH_3$,
$CH=NOH$,
CHO,
$CH_2OCH_3$,
$CH_2OH$,
Cl,
CN,
$COCF_3$,
$COC_1$–$C_3$ alkyl,
$CONH_2$,
$CONHC_1$–$C_3$ alkyl,
$CON(C_1$–$C_3$ alkyl$)_2$,
$COOC_1$–$C_3$ alkyl,
COOH,
F,
I,
$NH_2$,
$NHC_1$–$C_3$ alkyl,
$N(C_1$–$C_3$ alkyl$)_2$,
NHCHO,
$NHCOCH_3$,
$NHCONH_2$,
$NHSO_2CH_3$,
$NO_2$,
$OC_1$–$C_3$ alkyl,
$OCOCH_3$,
OH,
$SC_1$–$C_3$ alkyl,
$SOC_1$–$C_3$ alkyl,
$SO_2C_1$–$C_3$ alkyl,
$SO_2NH_2$,
$SO_2NHC_1$–$C_3$ alkyl,
$SO_2N(C_1$–$C_3$ alkyl$)_2$, and
$SO_3H$;
wherein A is selected from the group consisting of N and C;
wherein $R_1$ is an atom of hydrogen or $R_1$ is a $C_1$ to $C_4$ saturated, unsaturated, acyclic, cyclic or mixed hydrocarbyl or modified hydrocarbyl group and wherein, in the modified hydrocarbyl group,
  1 to 2 atoms of carbon may be replaced by 1 to 2 of the same or different heteroatoms selected from the group consisting of N, O, S, Cl, Br and I, and 1 to 3 atoms of hydrogen may be replaced by 1 to 3 atoms of fluorine;
wherein $R_2$ is a $C_2$ to $C_{13}$ saturated, unsaturated, acyclic, cyclic or mixed hydrocarbyl or modified hydrocarbyl group and wherein, in the modified hydrocarbyl group,
  1 to 4 atoms of carbon may be replaced by 1 to 4 of the same or different heteroatoms selected from the group consisting of N, O, S, Cl, Br and I, and 1 to 5 atoms of hydrogen may be replaced by 1 to 5 atoms of fluorine;

wherein $R_1$ and $R_2$ can be fused;

wherein $R_3$ is selected from the group consisting of H and $C_1$–$C_3$ alkyl; and wherein $R_4$ is selected from the group consisting of H and $CH_3$.

Sweetening agents according to the invention include tautomeric forms and physiologically acceptable salts of the above compounds. Further, the invention preferably comprises the compounds cited above with the proviso than when $X_3$, $X_5$, $R_3$ and $R_4$ are atoms of hydrogen, and when $X_4$ is CN or $NO_2$, that $R_1$ and $R_2$ may not be CN or $OCH_3$ and that when $X_4$ is H, $CF_3$, CHO, Cl, CN, $COCH_3$, F or $NO_2$ that $R_1$ may not be $NO_2$, $SOCH_3$ or $SOC_2H_5$ and that $R_2$ may not be $NO_2$, SOR, $SO_2R$, $SO_2NHR$ or $SO_2N(R)_2$, R being an alkyl, cycloalkyl or aryl group having up to 10 atoms of carbon, 1 or 2 of which may be replaced by 1 or 2 atoms of sulfur or oxygen.

It should be considered that by the term "modified hydrocarbyl" it is contemplated, as one example, that where $R_2$ is a $C_2$ modified hydrocarbyl group that one atom of carbon may be replaced by an atom of nitrogen so that the $C_2$ hydrocarbyl moiety may be replaced by the —CN cyano moiety. As a further example, it is contemplated that where $R_2$ is a $C_3$ modified hydrocarbyl group that one atom of carbon may be replaced by a nitrogen atom and two atoms of carbon may be replaced by two atoms of oxygen so that a $C_3$ hydrocarbyl moiety may be replaced by the —$NO_2$ nitro moiety. Other replacements of hydrocarbyl carbons by the same or different heteroatoms selected from the group consisting of N, O, S, Cl, Br, and I are similarly contemplated by the invention.

It should also be considered that the limitation that $R_2$ is a $C_2$ to $C_{13}$ group is established as a consequence of solubility limitations. It is contemplated that $R_2$ may be longer than the 13 carbon limitation stated above where other portions of the sweetening agent molecule or of the $R_2$ chain itself may be modified so as to provide for greater solubility.

Preferably, the sweetening agent is one wherein A is N, $R_4$ is H, $R_3$ is selected from the group consisting of H and $CH_3$, and $R_1$ is selected from the group consisting of H and $CH_3$. The sweetening agents are also preferably those wherein $X_3$ and $X_5$ are selected from the group consisting of H, Br, $CF_3$, $CH_3$, Cl and F. The agents are also preferably those wherein $X_4$ is selected from the group consisting of H, CN, $COOCH_3$, F and $NO_2$.

The sweetening agents are also preferably those wherein $R_2$ is selected from the group consisting of normal alk(en)(yn)yl $C_2$–$C_{13}$,
branched alk(en)(yn)yl $C_3$–$C_{13}$,
cycloalk(en)yl $C_3$–$C_{13}$,
alk(en)yl cycloalk(en)yl $C_4$–$C_{13}$,
cycloalk(en)yl alk(en)yl $C_4$–$C_{13}$,
alk(en)yl cycloalk(en)yl alk(en)yl $C_5$–$C_{13}$,
alk(en)yl bicycloalk(en)yl $C_7$–$C_{13}$,
fused bicycloalk(en)yl $C_7$–$C_{13}$,
alk(en)yl fused bicycloalk(en)yl $C_8$–$C_{13}$, fused bicycloalk(en)yl alk(en)yl $C_8$–$C_{13}$,
alkenyl fused bicycloalk(en)yl alk(en)yl $C_9$–$C_{13}$,
fused tricycloalk(en)yl $C_{10}$–$C_{13}$,
alk(en)yl fused tricycloalk(en)yl $C_{11}$–$C_{13}$, fused tricycloalk(en)yl alk(en)yl $C_{11}$–$C_{13}$ and
alk(en)yl fused tricycloalk(en)yl alk(en)yl $C_{13}$.

Particularly preferred are those sweetening agents wherein $R_2$ is selected from the group consisting of n-$C_5H_{11}$, n-$C_6H_{13}$, n-$C_7H_{15}$,
$CH(CH_3)(CH_2)_2CH_3$, $CH(CH_3)(CH_2)_3CH_3$, $(CH_2)_3CH(CH_3)_2$, $(CH_2)_4CH(CH_3)_2$, $(CH_2)_5CH(CH_3)_2$,
$C_6H_5$, $C_6$–$C_{10}$ cycloalkyl,
$CH_2C_6H_5$, $CH_2$-c-$C_6H_{11}$, $CH(CH_3)C_6H_5$, $CH(CH_3)$-c-$C_6H_{11}$, $(CH_2)_2C_6H_5$, $(CH_2)_2$-c-$C_6H_{11}$, $CH(CH_3)CH_2C_6H_5$, $CH(CH_3)CH_2$-c-$C_6H_{11}$,
$C_6H_4(CH_3)$, $C_6$–$C_{10}$ cycloalkyl($CH_3$),
$CH_2C_6H_4(CH_3)$, $CH_2$-c-$C_6H_{10}(CH_3)$, $CH(CH_3)C_6H_4(CH_3)$, $CH(CH_3)$-c-$C_6H_{10}(CH_3)$,
$(CH_2)_2CH(c-C_3H_5)_2$, $(CH_2)_3CH(c-C_3H_5)_2$, $CH(CH_3)CH_2CH(c-C_3H_5)_2$, $CH(CH_3)(CH_2)_2CH(c-C_3H_5)_2$, naphthyl, 5,6,7,8-tetrahydronaphthyl, perhydronaphthyl, indenyl, indanyl, naphthyl($CH_3$), 5,6,7,8-tetrahydronaphthyl($CH_3$), perhydronaphthyl($CH_3$), indenyl($CH_3$), indanyl($CH_3$), fenchyl, $CH_2$-naphthyl, $CH_2$-5,6,7,8-tetrahydronaphthyl, $CH_2$-perydronaphthyl, $CH_2$-indenyl, $CH_2$-indanyl, $CH_2$-naphthyl($CH_3$), $CH_2$-5,6,7,8-tetrahydronaphthyl($CH_3$), $CH_2$-perydronaphthyl($CH_3$), $CH_2$-indenyl($CH_3$), $CH_2$-indanyl($CH_3$), adamantyl,
$CH_2$-adamantyl, $CH(CH_3)$adamantyl, and
$CH_2$-adamantyl($CH_3$).

Preferred sweetening agents also include those listed above wherein $R_2$ is a modified hydrocarbyl group wherein up to four carbon atoms may be replaced by the same or different heteroatoms selected from a group consisting of S to replace C or $CH_2$, N to replace CH, NH and O to replace $CH_2$ and Cl, Br and I to replace $CH_3$ and wherein up to 5 atoms of hydrogen may be substituted by fluorine atoms. Also preferred are those sweetening agents wherein $R_2$ is selected from the group consisting of $H(CH_3)C_6H_5$, pyridinyl, piperidyl, homopiperidyl, indolyl, indolinyl, isoindolinyl, quinolyl, isoquinolyl, pyrazinyl, pyrimidyl, indazolyl, quinoxalinyl, quinazolinyl, purinyl, $OCH_2C_6H_5$, pyranyl, benzofurnayl, methoxyphenyl, methyloxycarbonylphenyl, 3,4-methylenedioxyphenyl, morpholinyl, benzoxazolyl, acetamindophenyl, cyano, nitro, thiophenyl, benzothiophenyl, 2,2,4,4-tetramethylthiacyclobut-3-yl, thiazolyl, isothiazolyl, $SO_2C_6H_5$, $SO_2C_6H_{11}$, $SO_2C_7H_{13}$, chlorophenyl, fluorophenyl and trifluoromethylphenyl.

Other preferred compounds include those having the formula

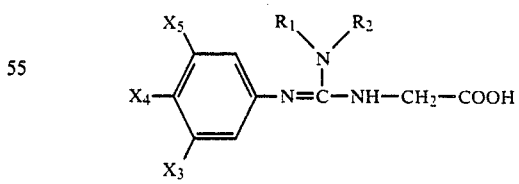

wherein $R_1$ is H or wherein $R_1$ is $CH_3$. Particularly preferred are such compounds wherein $X_3$ and $X_5$ are H and $X_4$ is CN or wherein $X_3$ and $X_5$ are selected from the group consisting of $CF_3$, $CH_3$, Cl and F and wherein $X_4$ is selected from the group consisting of H and CN. Other particularly preferred compounds include those wherein $R_2$ is selected from the group consisting of $CH(CH_3)C_6H_5$, $CH_2C_6H_5$, $CH(CH_3)$-c-$C_6H_{11}$, c-

$C_6H_{11}$, c-$C_7H_{13}$, c-$C_8H_{15}$, c-$C_9H_{17}$, c-$C_{10}H_{19}$, $SO_2C_6H_5$ and $SO_2C_7H_{13}$.

Most preferred are such compounds wherein $R_1$ is selected from the group consisting of H and $CH_3$; $R_3$ and $R_4$ are H; wherein $X_3$ and $X_5$ are H and $X_4$ is CN or wherein $X_3$ and $X_5$ are selected from the group consisting of $CF_3$, $CH_3$, Cl, H and F and wherein $X_4$ is selected from the group consisting of H and CN; and wherein $R_2$ is selected from the group consisting of $CH(CH_3)C_6H_5$, $CH_2C_6H_5$, $CH(CH_3)$-c-$C_6H_{11}$, c-$C_6H_{11}$, c-$C_7H_{13}$, c-$C_8H_{15}$, c-$C_9H_{17}$, c-$C_{10}H_{19}$, $SO_2C_6H_5$ and $SO_2C_7H_{13}$. Specifically preferred compounds include N-[N-cyclononylamino(4-cyanophenylimino)methyl]-2-aminoethanoic acid ($R_1$, $X_3$ and $X_5$ are H; $X_4$ is CN and $R_2$ is c-$C_9H_{17}$); N-[N-cyclooctylamino(4-cyanophenylimino)methyl]-2-aminoethanoic acid ($R_1$, $X_3$ and $X_5$ are H, $X_4$ is CN and $R_2$ is c-$C_8H_{15}$); N-[N-(S)-α-methylbenzylamino(3,5-dichlorophenylimino)methyl]-2-aminoethanoic acid ($R_1$ and $X_4$ are H, $X_3$ and $X_5$ are Cl and $R_2$ is (S)$CH(CH_3)CH_6H_5$); N-[N-cyclooctylamino(3-chloro-4-cyanophenylimino)methyl]-2-aminoethanoic acid ($R_1$ and $X_5$ are H, $X_3$ is Cl, $X_4$ is CN and $R_2$ is c-$C_8H_{15}$); N-[N-cyclooctylamino)4-cyano-3-methylphenylimino)methyl]-2-aminoethanoic acid ($R_1$ and $X_5$ are H, $X_3$ is $CH_3$, $X_4$ is CN and $R_2$ is c-$C_8H_{15}$); N-[N-benzylamino(3,5-dichlorophenylimino)methyl]-2-aminoethanoic acid ($R_1$ and $X_4$ are H, $X_3$ and $X_5$ are Cl and $R_2$ is $CH_2C_6H_5$); N-[N-methyl-N-benzylamino(3,5-dichlorophenylimino)methyl]-2-aminoethanoic acid ($R_1$ is $CH_3$, $X_4$ is H, $X_3$ and $X_5$ are Cl and $R_2$ is $CH_2C_6H_5$); N-[N-(S)-1-cyclohenxylethylamino(3,5-dichlorophenylimino) methyl]-2-aminoethanoic acid ($R_1$ and $X_4$ are H, $X_3$ an $X_5$ are Cl and $R_2$ is (S)$CH(CH_3)$-c-$C_6H_{11}$); N-[N-(S)-α-methylbenzylamino(4-cyanophenylimino)methyl]-2-aminoethanoic acid ($R_1$, $X_3$ and $X_5$ are H, $X_4$ is CN and $R_2$ is (S)$CH(CH_3)C_6H_5$) and N-[N-cycloheptylamino(3,5-dichlorophenylino)methyl]-2-aminoethanoic acid ($R_1$ and $X_4$ are H, $X_3$ and $X_5$ are Cl and $R_2$ is c-$C_7H_{13}$).

Preferred sweetening agents of the invention also include those wherein the agent is selected from the group of physiologically acceptable salts consisting of hydrochloride, sodium, potassium, ammonium, calcium and magnesium salts.

Also provided by the present invention is a process for sweetening foods, beverages, confectionaries, chewing gums, pharmaceuticals, veterinary preparations and toilet, cosmetic and hygiene products and the preparations so sweetened. The invention further comprises sweetening compositions characterized in that they comprise an effective amount of the high potency sweetening agents and a physiologically acceptable carrier which may be a bulking agent. Preferred carriers may be selected from the group consisting of polydextrose, starch, maltodextrins, cellulose, methylcellulose, carboxymethylcellulose, hydroxymethylcellulose, microcrystalline cellulose, sodium alginate, pectins, gums, lactose, maltose, glucose, leucine, glycerol, mannitol, sorbitol, sodium bicarbonate and phosphoric citric, tartaric, fumaric, benzoic, sorbic, propionic acids and their sodium, potassium and calcium salts and mixtures of all of the above.

Also provided by the invention are sweetening compositions characterized in that they comprise (1) a sweetening agent according to the invention and (2) a different sweetening agent. The different sweetening agent may be a sugar or a high potency sweetening agent and may specifically be selected from the group consisting of sucrose, corn syrups, fructose, aspartame, alitame, neohesperidine dihydrochalcone, hydrogenated isomaltulose, stevioside, L-sugars, glycyrrhizin, xylitol, acesulfam-K, saccharin (sodium, potassium or calcium salt), cyclamic acid (sodium, potassium or calcium salt), trichlorogalactosucrose, monellin and thaumatin and mixtures thereof.

The invention is thus seen to relate to improved derivatives of "suosan" which are characterized in particular by the replacement of the ureido or thioureido groups by guanidino, guanidinium or ethanamidino groups.

This improvement unexpectedly presents the advantage not only of conserving a sweet taste for these new compounds, but also of enhancing the sweetening power with respect to that of the ureido or thioureido derivatives, since compounds are obtained by this improvement which are up to 200,000 (two hundred thousand) times more potent than sucrose relative to a 2% sucrose solution.

The improvement also makes possible the elimination of the bitter of liquorice aftertastes which the corresponding ureido or thioureido derivatives of suosan frequently possess and which are characteristic, as well, of glycyrrhizin and thaumatin. In addition, the sweeteners fail to suffer from the metallic aftertaste of saccharin or acesulfame-K. In fact, new sweeteners obtained according to the invention are substantially indistinguishable from sucrose in their organoleptic properties. Preferred new sweetener agents according to the new invention are further characterized by improved solubility and stability characteristics.

The invention also relates to the process of sweetening a product (and to the products thus sweetened) by adding thereto an effective amount of the sweetening agents of the invention. "Effective amount" means the quantity which could be detected as sweet by the physiologic senses of the human species. Additionally, the invention relates to any composition including such a sweetening agent associated with a compatible carrier or with another sweetening agent. Mixtures of the present sweetening agents can also be employed in practicing the present invention.

DETAILED DESCRIPTION

The high potency sweetening agents of the present invention may be prepared through use of novel synthetic methods utilizing specific techniques which have been disclosed in the literature. These techniques have been summarized in a recent paper by Maryanoff (C. Maryanoff, R. C. Stanzione, J. N. Plampin, and J. E. Mills, J. Org. Chem. 1986, 51, 1882–1884). The techniques are further described in J. Med. Chem., 1978, no. 21, pp. 773–781; Chem. Ber. 1966, no. 99, 1252–157; U.K. Pat. No. 1587 258; J. Org. Chem., 1970, no. 35, pp. 2067–2069; J. Org. Chem. 1986, no. 56, 1882–1884; Chem. Ber. 1967, no. 100, pp. 591–604; J. fur Prakt. Chem. 1977, no. 319, pp. 149–157; and The Chemistry of Amidines and Imidates, S. Patai, ed. Wiley-Interscience 1975, pp. 283–348. Two general techniques are particularly useful. The first involves formation of an isothiourea intermediate while the second involves transformation of a carbodiimide intermediate.

According to the isothiourea method, an intermediate carrier of a group or easily liberated activating atom, designated by the letter L in the following reactants, can be employed. The group of easily liberated activating atoms is preferably selected from the compounds comprising the S-alkyl, O-alkyl, OSO$_2$-aryl, SO$_3$H and halogen groups. As a general principle, a reaction is brought about between the reactant intermediary and the appropriate complementary amine, that is to say, the following compounds are brought into contact with one another:

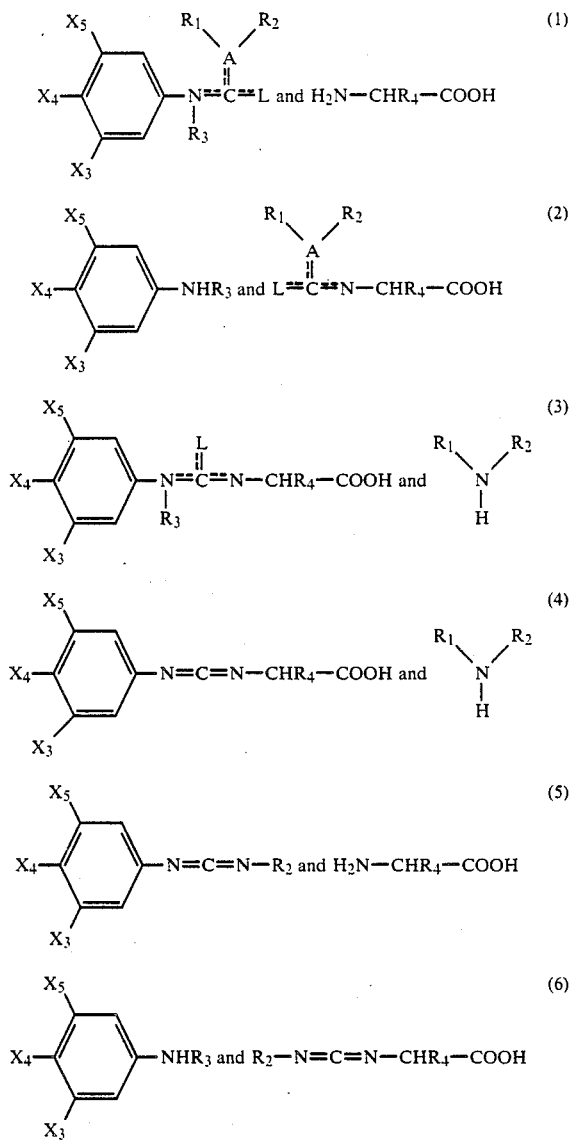

In the above formulas, X$_3$, X$_4$, X$_5$, A, R$_2$, R$_3$ and R$_4$ correspond to the definitions given previously and, as already stated, L represents the activating group.

These reactions can be carried out in water or in organic solvents such as ethanol, methanol, acetone, chloroform, carbon tetrachloride or pyridine at a temperature which may vary from ambient temperature to boiling. The choice of the solvent and the temperature employed will depend on the L group and the reactivity of the amine employed.

In certain reactions (reactions 2, 3, 4, 5 and 6), it may be preferable to provide the carboxyl group of the alpha-amino acid with initial protection in the form of an ester for example (methyl, ethyl, tert-butyl or benzyl ester). In this case, in order to obtain the compounds according to the present invention, it will be necessary to eliminate the protective group by the most appropriate means, which may be by saponification with a sodium hydroxide solution, or alternatively by hydrolysis with a hydrogen chloride solution, for example.

Various methods may be employed to prepare the intermediaries but the corresponding thiourea derivative will generally have to be prepared as follows, for example:

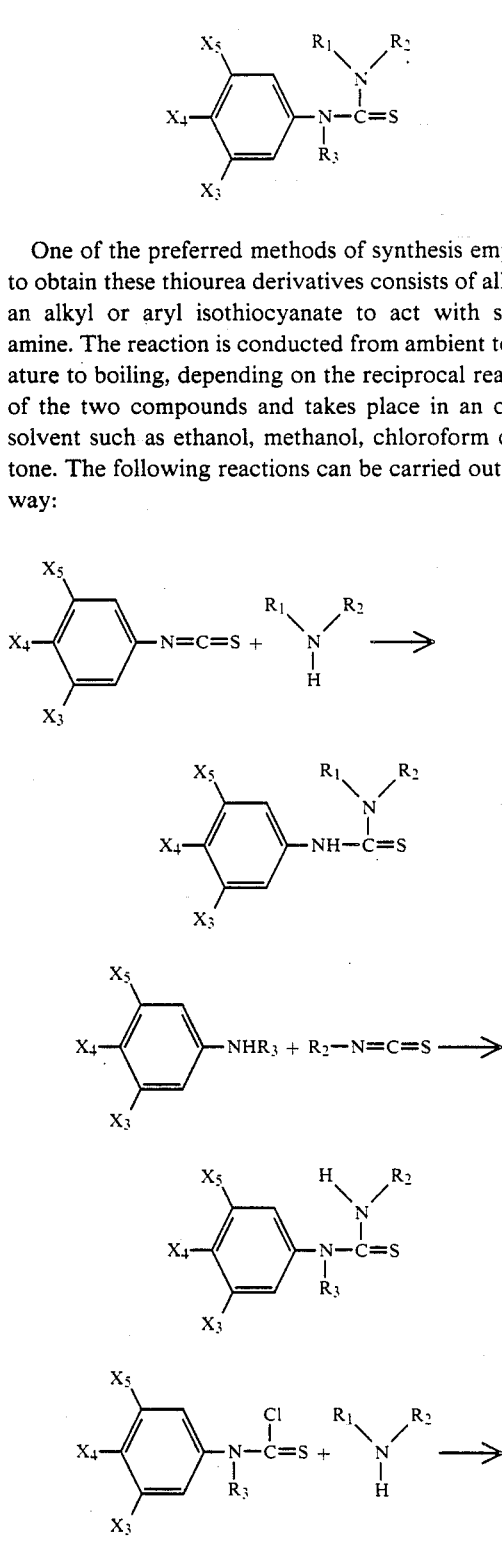

One of the preferred methods of synthesis employed to obtain these thiourea derivatives consists of allowing an alkyl or aryl isothiocyanate to act with suitable amine. The reaction is conducted from ambient temperature to boiling, depending on the reciprocal reactivity of the two compounds and takes place in an organic solvent such as ethanol, methanol, chloroform or acetone. The following reactions can be carried out in this way:

-continued

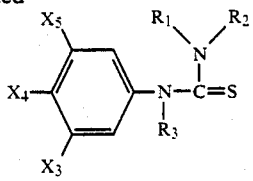

The preferred method consists of transforming thiourea derivatives obtained in this way into S-alkyl derivatives. The preferred L activating group is the S—CH₃ group, such as in the following compound, for example (when R₃=H):

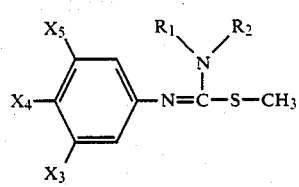

These intermediates are obtained by treating the corresponding thiourea derivative with an alkyl agent (such as methyl iodide or dimethyl sulfate) in solution in an organic solvent such as acetone or 2-butanone at a room temperature ranging from ambient temperature to boiling depending upon reactivity of the materials. The S-methylisothiourea derivatives are thus obtained in the form of salts (iodide or sulfate). These salts are next treated in a solution of sodium hydroxide or potassium hydroxide in order to free their base form. They are next condensed with alpha-amino acid in an ethanol and water mixture in the presence of a base such as sodium hydroxide, potassium hydroxide or a tertiary amine such as triethylamine, at a temperature ranging from ambient to boiling depending on reactivity of the materials.

Method 1: The Isothiourea Route:

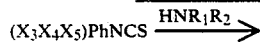

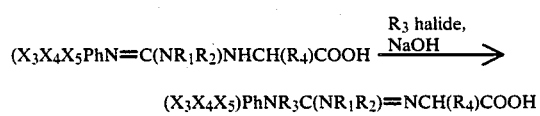

$(X_3X_4X_5)PhNR_3C(NR_1R_2)$=$NCH(R_4)COOH$

According to this general method, an alkyl or aryl isothiocyanate $(X_3X_4X_5)PhNCS$ is allowed to condense with an amine $HNR_1R_2$ preferably at ambient temperature and in an organic solvent to yield a thiourea $(X_3X_4X_5)$-$PhNCSNR_1R_2$. The thiourea is purified by recrystallization or other standard procedures and is then methylated with methyl iodide or dimethyl sulfate. This reaction is conducted in an organic solvent (e.g., acetone) at temperatures varying from ambient to 100° C. depending on thiourea reactivity. With methyl iodide, a crystalline isothiouronium salt, e.g., $[(X_3X_4X_5)PhN$=$C(NR_1R_2)SCH_3]^+I^-$, is thus obtained which is dissolved in water and treated with one molar equivalent of NaOH. The isothiourea $(X_3X_4X_5)PhN$=$C(NR_1R_2)SCH_3$ is then obtained by methylene chloride extraction and recrystallization. The isothiourea is then reacted with the amino acid $H_2NCH(R_4)COOH$ to give the guanidine $(X_3X_4X_5)PhN$=$C(NR_1R_2)NHCH(R_4)COOH$. This reaction may be conducted in water or organic solvents and at temperatures varying from ambient to 100° C. depending on the characteristics of $H_2NCH(R_4)COOH$. The guanidine is then purified by recrystallization or other standard methods. Pentasubstituted guanidine $(X_3X_4X_5)PhNR_3C(NR_1R_2)$=$NCH(R_4)COOH$ may be obtained on reaction of the tetrasubstituted guanidines with alkylating agents in organic solvents.

The second general method is based on the use of a carbodiimide intermediate which may be obtained by the action of phosgene or by an equimolecular mixture of triphenylphosphine, tertiary amine and carbon tetrachloride in an organic solvent, such as carbon tetrachloride or dichloromethane, at a temperature ranging from ambient temperature to boiling.

Method 2: The Carbodiimide Route:

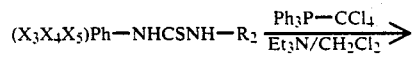

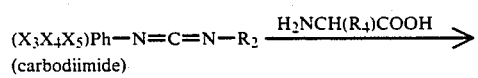

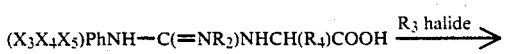

$(X_3X_4X_5)PhNR_3$—$C(NR_1R_2)$=$NCH(R_4)COOH$

According to this general method, an aryl isothiocyanate $(X_3X_4X_5)Ph$—NCS is allowed to condense with a primary amine $(R_2$—$NH_2)$ to yield an N,N'-disubstituted thiourea $(X_3X_4X_5)Ph$—NHCS—$NHR_2$. After purification by standard techniques such as recrystallization or chromatography, the thiourea is then converted to a carbodiimide $(X_3X_4Xhd\ 5)Ph$—NCN—$R_2$ on reaction in refluxing dichloromethane with one equivalent each of triphenylphosphine, carbon tetrachloride and triethylamine. The carbodiimide is not isolated but rather the carbodiimide solution is reacted directly with $H_2NCH(R_4)COOH$ to give the trisubstituted guanidine $(X_3X_4X_5)PhHN$—$C($=$NR_2)NHCH(R_4)COOH$. Tetra and pentasubstituted guanidines may be obtained on further alkylation of the trisubstituted guanidine with alkyl halides.

The present sweetening agents may exist as an equilibrium mixture of tautomeric forms. The sweetening agents are shown in the general formula as the tautomer with C=AR₁R₂ unsaturation; however, this tautomer is invariably in equilibrium with the tautomers, with $(X_3Xhd\ 4Xhd\ 5)PhN$=$C$ when R₃=H and C=NCH(R₄)COOH. Depending on the nature of R₁, R₂, R₃ and A, the sweetening agents according to the present invention may exist in Zwitterion or in acid form. They can thus be converted into salts by acids or by physiologically acceptable organic or inorganic bases. One of the best methods of preparing such salts consists of concentrating to dryness in vacuo a mixture of a compound according to the present invention in an aqueous solution with an equivalent amount of an acid or of an organic or inorganic base. The preferred salts according to the present invention are hydrochloride or sodium, potassium, ammonium, calcium or magnesium salts.

The present sweetening agents may take the form of a balanced mixture of tautomeric forms. Thus, the following tautomeric forms may be obtained, when $A=N$ and $R_1$, $R_3=H$:

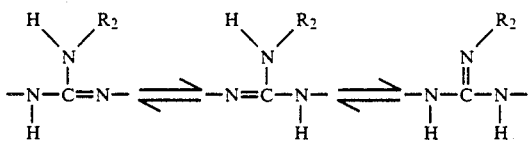

For instance, when $A=N$, $R_1=CH_3$ and $R_3=H$:

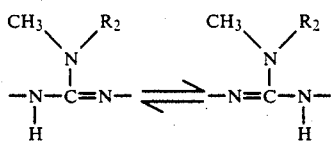

or when $A=N$, $R_1=H$ and $R_3=CH_3$:

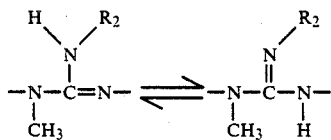

When $A=C$ and $R_3=H$, the following will apply, for example:

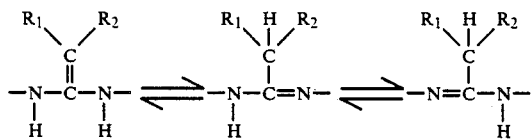

This is why the sweetening agents according to the present invention are represented in the general formula by a resonance hybrid and by one of the tautomeric forms in the descriptive part of the present patent, in the full knowledge that the tautomeric form must necessarily be in balance with the other tautomeric forms, depending on the nature of the substituents $X_3$, $X_4$, $X_5$, $R_1$, $R_2$ and $R_3$ as well as on the pH.

The sweetening agents of the present invention are added to any comestible product in which it is desired to have a sweet taste. The present sweetening agents are added to such products in amounts effective to impart the desired level of sweetness. The optimum amount of sweetening agent will vary depending on a variety of factors such as, for example, the sweetness potency of the particular sweetening agent, storage and use conditions of the product, the particular components of the products, the flavor profile of the comestible products and the level of sweetness desired. One skilled in the art can readily determine the optimum amount of sweetening agent to be employed in a particular formation of a comestible product by conducting routine sweetness (sensory) experiments. Usually, the present sweetening agents are added to the comestible products in amounts of from about 0.0001 to about 0.2 percent by weight of their comestible product, advantageously from about 0.0005 to about 0.15 weight percent and preferably from about 0.001 to about 0.1 weight percent. Concentrates, of course, will contain higher percentages of sweetening agent(s), and are diluted for end use purposes.

Suitable products which are sweetened by the present sweetening agents include any products for which a sweet flavor component is desired and includes food products (for human or animal consumption), beverages (alcoholic, soft drinks, juices, carbonated beverages), confectionary products (candies, chewing gum, baked goods, pastries, breads, etc.), hygiene products, cosmetics, pharmaceutical products and veterinary products.

The present sweetening agents can be added in pure form to comestible products to impart a sweet flavor. However, because of the high sweetness potency of the present sweetening agents, they are typically admixed with a carrier or bulking agent. Suitable carriers or bulking agents include polydextrose, starch, maltodextrine, cellulose, methylcellulose, carboxymethylcellulose, hydroxymethylcellulose, microcrystalline cellulose, cellulose derivatives, sodium alginate, pectins, gums, lactose, maltose, glucose, leucine, glycerol, mannitol, sorbitol, sodium bicarbonate and phosphoric, citric, tartaric, fumaric, benzoic, sorbic and propionic acids and their sodium, potassium and calcium salts and mixtures of all of the above.

The present sweetening agents can be employed alone as the sole sweetening agent in a comestible product or mixtures of two or more of the present sweetening agents can be employed to sweeten comestible products. Additionally, the present sweetening agents can be used in combination with other sweetening agents such as sugars (such as sucrose and fructose), corn syrups, dipeptide sweeteners such as aspartame and alitame and other sweeteners such as glycyrrhizin, xylitol, sorbitol, mannitol, acesulfam K, thaumatin, monellin, cyclamates, saccharin, neohesperidin dihydrochalcone, hydrogenated isomaltulose, steveioside, L-sugars, trichlorogalactosucrose, and mixtures thereof.

The sweetening potency of the compounds prepared in the following examples was assessed by a panel of up to six trained tasters. To this end, the compounds, in aqueous solution at variable concentrations, are compared, from the standpoint of taste, with control solutions of sucrose at concentrations of 2% or of 2%, 5%, and 10% respectively, i.e., at concentrations corresponding to those used currently in the food and beverage industry. The sweetening potency of the synthetic sweeteners varies depending on the concentration of the solution of sucrose used as reference. The sweetening potency of the compound tested with respect to sucrose thus corresponds to the ratio by weight which exists between the compound and the sucrose at equal sweetening intensity, i.e., when the sweet taste between the solution of the compound tested and the control solution of sucrose are considered, by a majority of tasters, to have the same sweetening intensity.

The present invention includes those compounds presenting substituents at positions 3 and 5 (meta substitution) on the phenyl group. The presence of particular substituents at these positions serves to enhance both the sweetening potency of the compounds and their thermal stability. It has been found that derivatives disubstituted by $CH_3$ or Cl at positions 3 and 5 (meta substitution) of the benzenic group are roughly 40 times sweeter on a weight basis than the same derivatives substituted only at position 4 (para substitution). It has moreover been observed that ortho-substitution of the phenyl group results in compounds which are either not at all sweet or which are only slightly sweet.

The manner in which the invention may be carried out and the advantages following therefore will be more readily seen from the following illustrative non-limiting examples. The compounds of the present invention described in the following examples and tables were purified by standard methods, such as recrystallization or chromatography. Structure and purity were verified by traditional techniques, such as thin layer chromatography, high performance liquid chromatography, IR spectrometry, nuclear magnetic resonance and elemental analysis.

EXAMPLE 1

Synthesis of N-[N-(S)-α-methylbenzylamino (phenylimino)methyl]-2-aminoethanoic acid

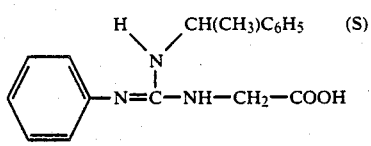

This compound is obtained from glycine and N-(S)-α-methylbenzyl-N'-phenyl-S-methylisothiourea according to the experimental procedure described in Example 2 (yield 53%, melting point 209° C.).

The sweetening power of this compound corresponds approximately, on a weight basis, to 5,000 (five thousand) times that of a 2% sucrose solution.

EXAMPLE 2

Synthesis of N-[N-(S)-α-methylbenzylamino (3-bromophenylimino)methyl]-2-aminoethanoic acid

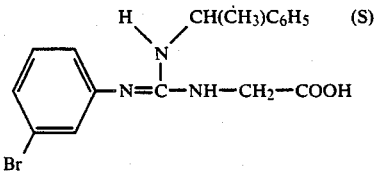

Step 1

Preparation of N-(S)-α-methylbenzyl-N'-(3-bromophenyl)thiourea

Five grams (41 mmol) of (S)-α-methylbenzylamine and 8 g (37 mmol) of 3-bromophenyl isothiocyanate are mixed in 50 cm³ of 95% ethanol. After stirring for 4 hours at 20° C., the solution is concentrated to dryness in vacuo. After washing with 200 cm³ of hexane, 11.6 g (yield 97%) of the thiourea derivative is obtained with a melting point of 103° C.

Step 2

Synthesis of N-(S)-α-methylbenzyl-N'-(3-bromophenyl)-S-metylisothiourea

A mixture of 11.5 g (34 mmol) of the compound obtained previously and 7.24 g (51 mmol) of methyl iodide is stirred for 10 hours in 100 cm³ of 2-butanone at 20° C. After concentrating the mixture to dryness in vacuo, the residue is triturated in 200 cm³ of ethyl ether and then separated by filtration. 15.1 g (yield 92%) of the S-methylisothiourea derivative is obtained in the form of hydroiodide. This salt is next dissolved in 200 cm³ of a 1N solution of sodium hydroxide. The resulting alkaline mixture is extracted with dichloromethane (3×100 cm³). After drying with anhydrous sodium sulfate, 9.5 g (yield 86%) of the S-methylisothiourea derivative is obtained in the form of a colorless oil.

Step 3

Preparation of the N-[N-(S)-α-methylbenzylamino)3-bromophenylimino)-methyl]-2-aminoethanoic acid A mixture of 3 g (40.8 mmol) of glycine and 1.6 g (40.8 mmol) of sodium hydroxide in 5 cm³ of water is added to a solution of 9.5 (27.2 mmol) of N-(S)-α-methylbenzyl-N'-(3-bromophenyl)-S-methylisothiourea in 100 cm³ of 95% ethanol. The mixture is heated to 70° C. for 20 hours. After cooling, the solution is concentrated to dryness and the residue is dissolved in 60 cm³ of water. The resulting solution is washed with dichloromethane (3×50 cm³) and then acidified with a 6 N HCl solution to bring its pH to 7. The desired guanidino derivative precipitates and is separated out by filtration. 6.4 (yield 62%) of the compound is obtained with a melting point of 212° C.

The sweetening power of this compound corresponds approximately, on a weight basis, to 25,000 (twenty-five thousand) times that of a 2% sucrose solution.

EXAMPLE 3

Synthesis of N-[N-(S)-α-methylbenzylamino(3-trifluoromethylphenylimino)methyl]-2-aminoethanoic acid

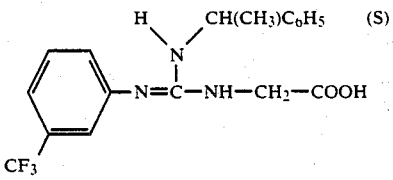

This compound is obtained from glycine and N-(S)-α-methylbenzyl-N'-(3-trifluoromethylphenyl)-S-methylisothiourea according to the experimental procedure described in Example 2 (yield 34%; melting point 158° C.).

The sweetening power of this compound corresponds approximately, on a weight basis, to 7,500 (seven thousand five hundred) times that of a 2% sucrose solution.

EXAMPLE 4

Synthesis of N-[N-(S)-α-methylbenzylamino(3-methylphenylimino)-methyl]-2-aminoethanoic acid

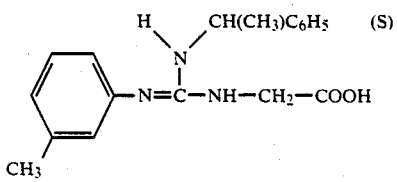

This compound is obtained from glycine and N-(S)-α-methylbenzyl-N'-(3-methylphenyl)-S-methylisothiourea according to the experimental procedure described in Example 2 (yield 28%; melting point 205° C.).

The sweetening power of this compound corresponds approximately, on a weight basis, to 12,000 (twelve thousand) times that of a 2% sucrose solution.

EXAMPLE 5

Synthesis of N-[N-(S)-α-methylbenzylamino(3-ethylphenylimino)methyl]-2-aminoethanoic acid

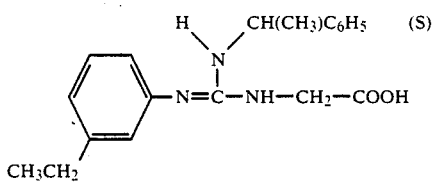

This compound is obtained from glycine and N-(S)-α-methylbenzyl-N'-(3-ethylphenyl)-S-methylisothiourea according to the experimental procedure described in Example 2 (yield 42%; melting point 205° C.).

The sweetening power of this compound corresponds approximately, on a weight basis, to 4,500 (four thousand five hundred) times that of a 2% sucrose solution.

EXAMPLE 6

Synthesis of N-[N-(S)-α-methylbenzylamino(3-chlorophenylimino)methyl]-2-aminoethanoic acid

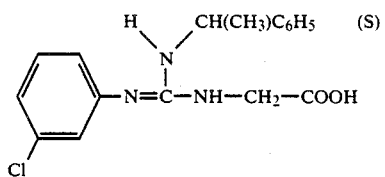

This compound is obtained from glycine and N-(S)-α-methylbenzyl-N'-(3-chlorophenyl)-S-methylisothiourea according to the experimental procedure described in Example 2 (yield 22%; melting point 178° C.).

The sweetening power of this compound corresponds approximately, on a weight basis, to 30,000 (thirty thousand) times that of a 2% sucrose solution.

EXAMPLE 7

Synthesis of N-[N-(S)-α-methylbenzylamino(3-cyanophenylimino)methyl]-2-aminoethanoic acid

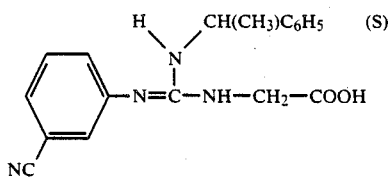

This compound is obtained from glycine and N-(S)-α-methylbenzyl-N'-(3-cyanophenyl)-S-methylisothiourea according to the experimental procedure described in Example 2 (yield 63%; melting point 190° C.).

The sweetening power of this compound corresponds approximately, on a weight basis, to 5,500 (five thousand five hundred) times that of a 2% sucrose solution.

EXAMPLE 8

Synthesis of N[N-(S)-α-methylbenzylamino(3-nitrophenylimino)methyl]-2-aminoethanoic acid

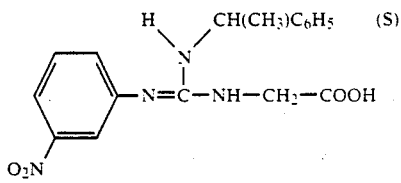

This compound is obtained from glycine and N-(S)-α-methylbenzyl-N'-(3-nitrophenyl)-S-methylisothiourea according to the experimental procedure described in Example 2 (yield 39%; melting point 195° C.).

The sweetening power of this compound corresponds approximately, on a weight basis, to 6,000 (six thousand) times that of a 2% sucrose solution.

EXAMPLE 9

Synthesis of N-[N-(S)-α-methylbenzylamino(3-methoxyphenylimino)methyl]-2-aminoethanoic acid

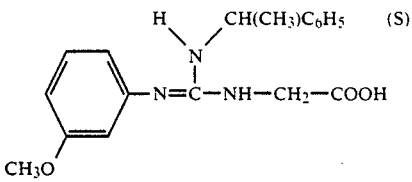

This compound is obtained from glycine and N-(S)-α-methylbenzyl-N'-(3-methoxyphenyl)-S-methylisothiourea according to the experimental procedure described in Example 2 (yield 78%; melting point 191° C.).

The sweetening power of this compound corresponds approximately, on a weight basis, to 4,500 (four thousand five hundred) times that of a 2% sucrose solution.

EXAMPLE 10

Synthesis of N-[N-(S)-α-methylbenzylamino(3-methylmercaptophenylimino)methyl]-2-aminoethanoic acid

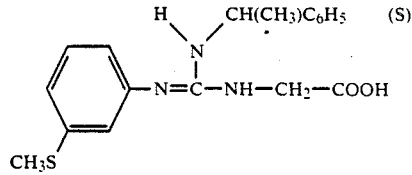

This compound is obtained from glycine and N-(S)-α-methylbenzyl-N'-(3-methylmercaptophenyl)-S-methylisothiourea according to the experimental procedure described in Example 2 (yield 59%; melting point 186° C.).

The sweetening power of this compound corresponds approximately, on a weight basis, to 5,500 (five thousand five hundred) times that of a 2% sucrose solution.

EXAMPLE 11

Synthesis of N-[N-(S)-α-methylbenzylamino(4-trifluoromethylphenylimino)methyl]-2-aminoethanoic acid

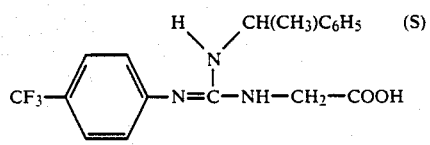

This compound is obtained from glycine and N-(S)-α-methylbenzyl-N'-(4-trifluoromethylphenyl)-S-methylisothiourea according to the experimental procedure described in Example 2 (yield 9%, melting point 168° C.).

The sweetening power of this compound corresponds approximately, on a weight basis, to 500 (five hundred) times that of a 2% sucrose solution.

EXAMPLE 12

Synthesis of N-[N-(S)-α-methylbenzylamino(4-methylphenylimino)-methyl]-2-aminoethanoic acid

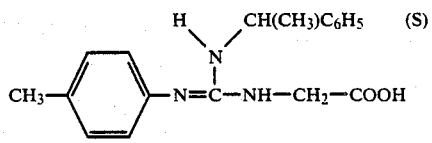

This compound is obtained from glycine and N-(S)-α-methylbenzyl-N'-(4-methylphenyl)-S-methylisothiourea, according to the experimental procedure described in Example 2 (yield 26%; melting point 137° C.).

The sweetening power of this compound corresponds approximately, on a weight basis, to 800 (eight hundred) times that of a 2% sucrose solution.

EXAMPLE 13

Synthesis of N-[N-(S)-α-methylbenzylamino(4-chlorophenylimino)-methyl]-2-aminoethanoic acid

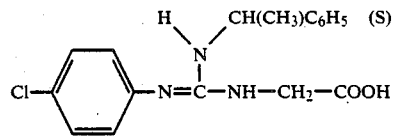

This compound is obtained from glycine and N-(S)-α-methylbenzyl-N'-(4-chlorophenyl)-S-methylisothiourea according to the experimental procedure described in Example 2 (yield 42%, melting point 146° C.).

The sweetening power of this compound corresponds approximately, on a weight basis, to 3,000 (three thousand) times that of a 2% sucrose solution.

EXAMPLE 14

Synthesis of N-[N-(S)-α-methylbenzylamino(4-cyanophenylimino)-methyl]-2-aminoethanoic acid

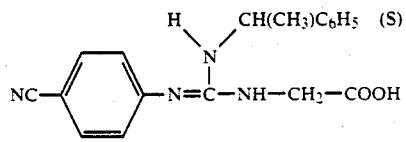

This compound is obtained from glycine and N-(S)-α-methylbenzyl-N'-(4-cyanophenyl)-S-methylisothiourea, following the experimental procedure described in Example 2 [yield 35%; $[\alpha]_D^{20} + 112.5°$ (c=1, 0.5N HCl); melting point 206° C.].

The sweetening power of this compound corresponds approximately, on a weight basis, to 28,000 (twenty-eight thousand) times that of sucrose relative to a 2% sucrose solution, to 20,000 (twenty thousand) relative to a 5% sucrose solution and to 10,000 (ten thousand) times relative to a 10% sucrose solution.

EXAMPLE 15

Synthesis of N-[N-(S)-α-methylbenzylamino(4-acetylphenylimino)-methyl]-2-aminoethanoic acid

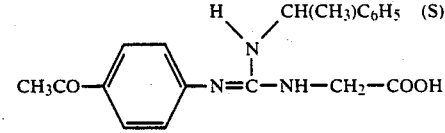

This compound is obtained from glycine and N-(S)-α-methylbenzyl-N'-(4-acetylphenyl)-S-methylisothiourea according to the experimental procedure of Example 2 (yield 24%, melting point 173° C.).

The sweetening power of this compound corresponding approximately, on a weight basis, to 800 (eight hundred) times that of a 2% sucrose solution.

EXAMPLE 16

Synthesis of N-[N-(S)-α-methylbenzylamino(4-methoxycarbonylphenylimino)methyl]-2-aminoethanoic acid

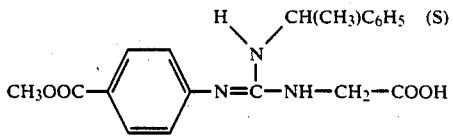

This compound is obtained from glycine and N-(S)-α-methylbenzyl-N'-(4-methoxycarbonylphenyl)-S-methylisothiourea according to the experimental procedure of Example 2 (yield 28%; melting point 163° C.).

The sweetening power of this compound corresponds approximately, on a weight basis, to 700 (seven hundred) times that of a 2% sucrose solution.

EXAMPLE 17

Synthesis of N-[N-(S)-α-methylbenzylamino(4-fluorophenylimino)-methyl]-2-aminoethanoic acid

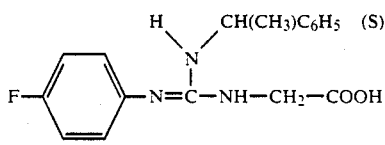

This compound is obtained from glycine and N-(S)-α-methylbenzyl-N'-(4-fluorophenyl)-S-methylisothiourea according to the experimental procedure of Example 2 (yield 15%, melting point 166° C.).

The sweetening power of this compound corresponds approximately, on a weight basis, to 4,000 (four thousand) times that of a 2% sucrose solution.

EXAMPLE 18

Synthesis of N-[N-(S)-α-methylbenzylamino(4-nitrophenylimino)-methyl]-2-aminoethanoic acid

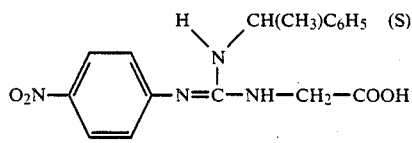

This compound is obtained from glycine and N-(S)-α-methylbenzyl-N'-(4-nitrophenyl)-S-methylisothiourea according to the experimental procedure described in Example 2 (yield 85%, melting point 198° C.).

The sweetening power of this compound corresponds approximately, on a weight basis, to 7,000 (seven thousand) times that of a 2% sucrose solution.

EXAMPLE 19

Synthesis of N-[N-(S)-α-methylbenzylamino(4-methoxyphenylimino)methyl]-2-aminoethanoic acid

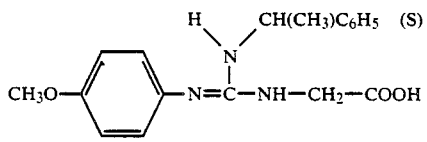

This compound is obtained from glycine and N-(S)-α-methylbenzyl-N'-(4-methoxyphenyl)-S-methylisothiourea according to the experimental procedure of Example 2 (yield 22%; melting point 195° C.).

The sweetening power of this compound corresponds approximately, on a weight basis, to 2,100 (two thousand one hundred) times that of a 2% sucrose solution.

EXAMPLE 20

Synthesis of N-[N-(S)-α-methylbenzylamino(4-hydroxyphenylimino)methyl]-2-aminoethanoic acid

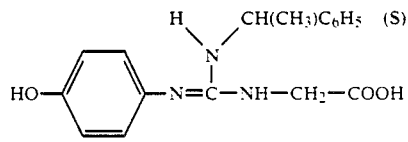

This compound is obtained from glycine and N-(S)-α-methylbenzyl-N'-(4-hydroxyphenyl)-S-methylisothiourea according to the experimental procedure described in Example 2 (yield 23%, melting point 160° C.).

The sweetening power of this compound corresponding approximately, on a weight basis, to 400 (four hundred) times that of a 2% sucrose solution.

EXAMPLE 21

Synthesis of N-[N-(S)-α-methylbenzylamino(4-methylmercaptophenylimino)methyl]-2-aminoethanoic acid

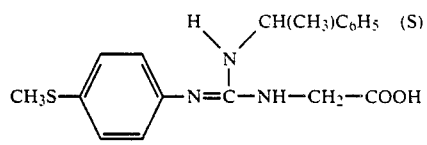

This compound is obtained from glycine and N-(S)-α-methylbenzyl-N'-(4-methylmercaptophenyl)-S-methylisothiourea according to the experimental procedure of Example 2 (yield 77%; melting point 171° C.).

The sweetening power of this compound corresponds approximately, on a weight basis, to 1,200 (one thousand two hundred) times that of a 2% sucrose solution.

EXAMPLE 22

Synthesis of N-[N-(S)-α-methylbenzylamino(4-cyano-3-methylphenylimino)methyl]-2-aminoethanoic acid

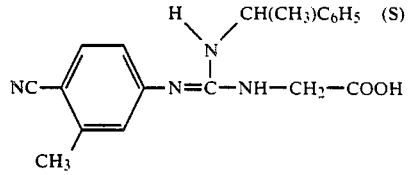

This compound is obtained from glycine and N-(S)-α-methylbenzyl-N'-(4-cyano-3-methylphenyl)-S-methylisothiourea according to the experimental procedure described in Example 2 (yield 46%, melting point 172° C.).

The sweetening power of this compound corresponds approximately, on a weight basis, to 50,000 (fifty thousand) times that of a 2% sucrose solution.

EXAMPLE 23

Synthesis of
N-[N-(S)-α-methylbenzylamino(3,4-dichloro-phenylimino)methyl]-2-aminoethanoic acid

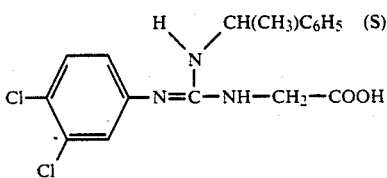

This compound is obtained from glycine and N-(S)-α-methylbenzyl-N'-(3,4-dichlorophenyl)-S-methylisothiourea according to the experimental procedure described in Example 2 (yield 20%; melting point 195° C.).

This sweetening power of this compound corresponds approximately, on a weight basis, to 17,000 (seventeen thousand) times that of a 2% sucrose solution.

EXAMPLE 24

Synthesis of
N-[N-(S)-α-methylbenzylamino(3-trifluoromethyl-5-methoxyphenylimino)methyl]-2-aminoethanoic acid:

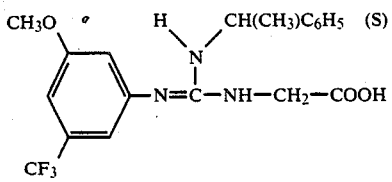

This compound is obtained from glycine and N-(S)-α-methylbenzyl-N'-(3-trifluoromethyl-5-methoxyphenyl)-S-methylisothiourea according to the experimental procedure described in Example 2 (yield 71%; melting point 192° C.).

The sweetening power of this compound corresponds approximately, on a weight basis, to 7,000 (seven thousand) times that of a 2% sucrose solution.

EXAMPLE 25

Synthesis of N-[N-(S)-α-methylbenzylamino(3,5-dimethylphenylimino)methyl]-2-aminoethanoic acid

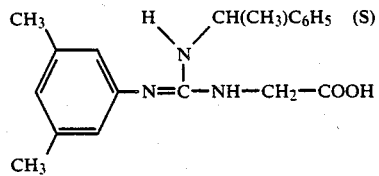

This compound is obtained from glycine and N-(S)-α-methylbenzyl-N'-(3,5 dimethylphenyl)-S-methylisothiourea according to the experimental procedure described in Example 2 (yield 67%; melting point 225° C.).

The sweetening power of this compound corresponds approximately, on a weight basis, to 30,000 (thirty thousand) times that of a 2% sucrose solution.

EXAMPLE 26

Synthesis of
N-[N-(S)-α-methylbenzylamino(3,5-dichloro-phenylimino)methyl]-2-aminoethanoic acid

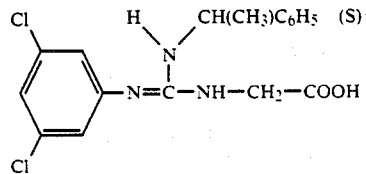

This compound is obtained from glycine and N-(S)-α-methylbenzyl-N'-(3,5-dichlorophenyl)-S-methylisothiourea according to the experimental procedure described in Example 2 (yield 46%; melting point 202° C.).

The sweetening power of this compound corresponds approximately, on a weight basis, to 120,000 (one hundred and twenty thousand) times that of a 2% sucrose solution, to 90,000 (ninety thousand) times the sweetening powder of a 5% sucrose solution and to 50,000 (fifty thousand) times the sweetening power of a 10% sucrose solution.

EXAMPLE 27

Synthesis of
N-[N-(S)-α-methylbenzylamino(3,5-disfluoro-phenylimino)methyl]-2-aminoethanoic acid

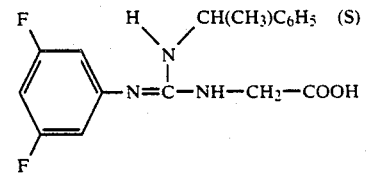

This compound is obtained from glycine and N-(S)-α-methylbenzyl-N'-(3,5-difluorophenyl)-S-methylisothiourea according to the experimental procedure described in Example 2 (yield 66%; melting point 212° C.).

The sweetening power of this compound corresponds approximately, on a weight basis, to 15,000 (fifteen thousand) times that of a 2% sucrose solution.

EXAMPLE 28

Synthesis of
N-[N-(S)-α-methylbenzylamino(3,4,5-trichloro-phenylimino)methyl]-2-aminoethanoic acid

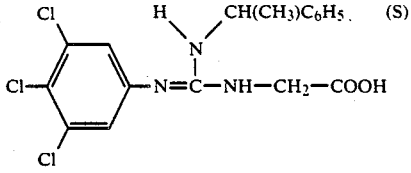

This compound is obtained from glycine and N-(S)-α-methylbenzyl-N'-(3,4,5-trichlorophenyl)-S-methylisothiourea according to the experimental procedure described in Example 2 (yield 69%; melting point 208° C.).

The sweetening power of this compound corresponds approximately, on a weight basis, to 35,000 (thirty-five thousand) times that of a 2% sucrose solution.

EXAMPLE 29

Synthesis of N-[2-nitro(3,5-dichlorophenylamino)ethenyl]-2-aminoethanoic acid

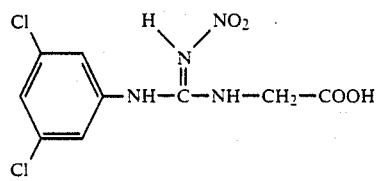

Five grams (30 mmol) of 1-nitro-2,2-(methylthio)ethene and 4.91 g (30 mmol) of 3,5-dichloroaniline are mixed together in 50 cm³ of 95% ethanol. The solution is heated at reflux for 6 hours. After cooling, the resulting precipitate is filtered, washed with ethyl ether (3×20 cm³). 5.3 g of 1-nitro-2-(3,5-dichlorophenylamino)-2-(methylthio)-ethene (yield 63%) are obtained with a melting point of 114° C.

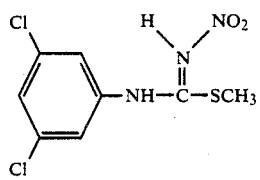

1.34 g (17.9 mmol) of glycine, 5 g (17.9 mmol) of 1-nitro-2-(3,5-dichlorophenylamino)-2-(methylthio)ethene are mixed together with 2.5 cm³ (17.9 mmol) of triethylamine in 50 cm³ of a 5:1 solution of ethanol in water. The mixture is heated at reflux for 2 hours. After concentration in vacuo, the residue is dissolved in 60 cm³ of a 1N sodium hydroxide solution. The resulting solution is washed with ethyl acetate (4×20 cm³) and then acidified in a 6 N HCl solution to bring its pH close to 7.

The resulting solid is filtered, washed with water (2×2 cm³) and dried in vacuo. 1.4 g of N-[2-nitro(3,5-dichlorophenylamino)ethenyl]-2-aminoethanoic acid (yield 26%) of the compound is obtained with a melting point of 207° C.

The sweetening power of this compound corresponds approximately, on a weight basis, to 400 (four hundred) times that of a 2% sucrose solution.

EXAMPLE 30

Synthesis of N-[2,2-dicyano(3,5-dichlorophenylamino)ethenyl]-2-aminoethanoic acid

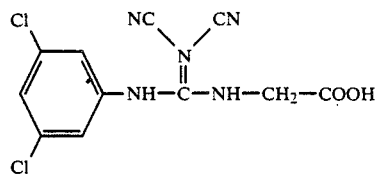

A 1.64 gram portion sodium hydride (in a 50% dispersion in liquid paraffin) is added in several fractions to a solution, cooled to 0° C., of 2.26 g (34 mmol) of malononitrile dissolved in 25 cm³ of dimethylformamide. The solution is next maintained at 10° C. for 10 minutes. Seven grams (34 mmol) of 3,5-dichlorophenyl isothiocyanate dissolved in 20 cm³ of dimethylformamide is then added to the solution. The reaction mixture is maintained at 20° C. for 15 minutes and then concentrated to dryness. After hot trituration in 5×50 cm³ of chloroform, the residue is dried in vacuo. Six grams of the solid obtained in this way and 2.84 g of dimethyl sulfate are dissolved in 200 cm³ of 95% ethanol and left in contact for 2 hours at 20° C. After elimination of the ethanol, the remaining solid is washed with water (4×50 cm³); 4.3 g of 1,1-dicyano-2-(3,5-dichlorophenylamino)-2-(methylthio)-ethene (yield 74%) are obtained after drying:

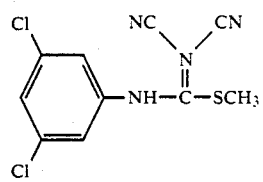

A 1.58 gram portion (21.1 mmol) of glycine and 4 g (21.1 mmol) of the compound obtained previously are mixed together with 2.7 g (21.1 mmol) of N,N-diisopropylethylamine in 200 cm³ of ethanol. The mixture is maintained at 70° C. for 24 hours. After concentration is vacuo, the residue is dissolved in 200 cm³ of an aqueous 2% sodium carbonate solution. The solution is washed with ethyl ether (3×50 cm³) and acidified with a 3N HCl solution. The resulting pasty precipitate is separated out by decantation. After purification by chromatography, 0.4 g of N-[2,2-dicyano(3,5-dichlorophenylamino) ethenyl]-2-aminoethanoic acid (yield 10%) is obtained with a melting point of 103° C.

The sweetness power of this compound corresponds approximately, on a weight basis, to 30 (thirty) times that of a 2% sucrose solution.

EXAMPLE 31

Synthesis of N-[N-methyl-N-benzylamino(3,5-dichllrophenylimino)methyl]-2-aminoethanoic acid

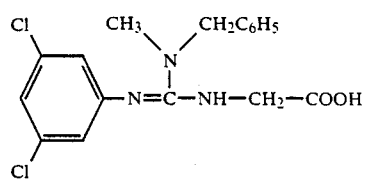

This compound is obtained from glycine and N-methyl-N-benzyl-N'-3,5-dichlorophenyl-S-methylisothiourea according to the experimental procedure described in Example 2 (yield 10%; melting point 153° C.).

The sweetening power of this compound corresponds approximately, on a weight basis, to 20,000 (twenty thousand) times that of a 2% sucrose solution.

EXAMPLE 32

Synthesis of
N-[N-methyl-N-1-methylethylamino(4-cyano-phenylimino)methyl]-2-aminoethanoic acid

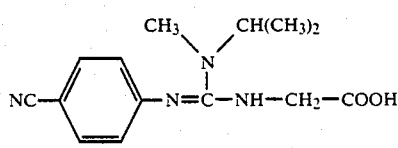

This compound is obtained from glycine and N-methyl-N-1-methylethyl-N'-(4-cyanophenyl)-S-methylisothiourea according to the experimental procedure of Example 2 (yield 5%, melting point 120° C.).

The sweetening power of this compound corresponds approximately, on a weight basis, to 80 (eighty) times that of a 2% sucrose solution.

EXAMPLE 33

Synthesis of
N-[N-methyl-N-benzylamino(4-cyanophenylimino)methyl]-2-aminoethanoic acid

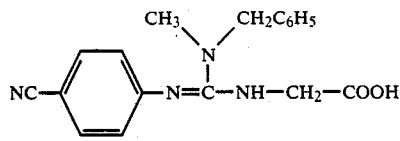

This compound is obtained from glycine and N-methyl-N-benzyl-N'-(4-cyanophenyl)-S-methylisothiourea, according to the experimental procedure described in Example 2 (yield 22%; melting point 133° C.).

The sweetening power of this compound corresponds approximately, on a weight basis, to 3,000 (three thousand) times that of sucrose relative to a 2% sucrose solution, to 1,800 (one thousand eight hundred) relative to a 5% sucrose solution and to 1,200 (one thousand two hundred) relative to a 10% sucrose solution.

EXAMPLE 34

Synthesis of
N-[N-ethyl-N-benzylamino(4-cyanophenylimino)methyl]-2-aminoethanoic acid

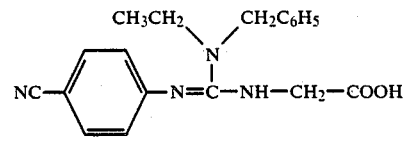

This compound is obtained from glycine and N-ethyl-N-benzyl-N'-(4-cyanophenyl)-S-methylisothiourea according to the experimental procedure of Example 2 (yield 5%, melting point 147° C.).

The sweetening power of this compound corresponds approximately, on a weight basis, to 3,000 (three thousand) times that of a 2% sucrose solution.

EXAMPLE 35

Synthesis of
N-[N-ethylamino(4-cyanophenylimino)methyl]-2-aminoethanoic acid

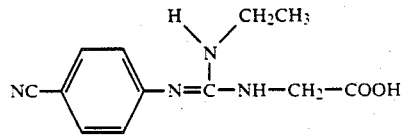

This compound is obtained from glycine and N-ethyl-N'-(4-cyanophenyl)-S-methylisothiourea according to the experimental procedure of Example 2 (yield 18%, melting point 185° C.).

The sweetening power of this compound corresponds approximately, on a weight basis, to 350 (three hundred fifty) times that of a 2% sucrose solution.

EXAMPLE 36

Synthesis of
N-[N-hexylamino(4-cyanophenylimino)methyl]-2-aminoethanoic acid

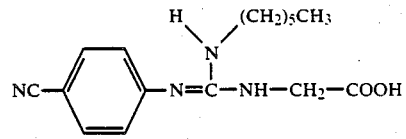

This compound is obtained from glycine and from N-hexyl-N'-(4-cyanophenyl)-S-methylisothiourea by following the experimental procedure described in Example 2 (yield 17%; melting point 159° C.).

The sweetening power of this compound corresponds approximately, on a weight basis, to 6,000 (six thousand) times that of sucrose relative to a 2% sucrose solution, to 4,300 (four thousand three hundred) times relative to a 5% sucrose solution and 1,400 (one thousand four hundred) times relative to a 10% sucrose solution.

EXAMPLE 37

Synthesis of
N-[N-(3-methylbutyl)amino(4-cyanophenylimino)methyl]-2-aminoethanoic acid:

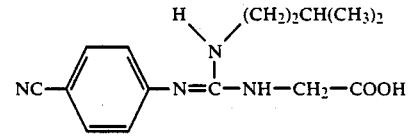

This compound is obtained from glycine and N-(3-methylbutyl)-N'-(4-cyanophenyl)-S-methylisothiourea according to the experimental procedure of Example 2 (yield 16%, melting point 192° C.).

The sweetening power of this compound corresponds approximately, on a weight basis, to 200 (two hundred) times that of a 2% sucrose solution.

EXAMPLE 38

Synthesis of N-[N-(1,1-dimethylpropyl)amino(4-cyanophenylimino)methyl]-2-aminoethanoic acid

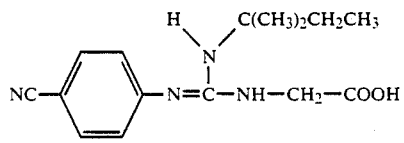

This compound is obtained from glycine and N-(1,1-dimethylpropyl)-N'-(4-cyanophenyl)-S-methylisothiourea according to the experimental procedure of Example 2 (yield 16%, melting point 210° C.).

The sweetening power of this compound corresponds approximately, on a weight basis, to 300 (three hundred) times that of a 2% sucrose solution.

EXAMPLE 39

Synthesis of N-[N-(1,1,3,3-tetramethylbutyl)amino(4-cyanophenylimino)methyl]-2-aminoethanoic acid

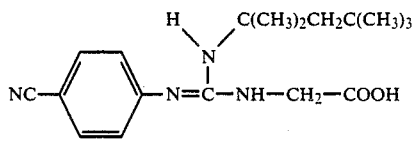

This compound is obtained from glycine and N-(1,1,3,3-tetramethylbutyl)-N'-(4-cyanophenyl)-S-methylisothiourea according to the experimental procedure described in Example 2 (yield 43%, melting point 189° C.).

The sweetening power of this compound corresponds approximately, on a weight basis, to 1,200 (one thousand two hundred) times that of a 2% sucrose solution.

EXAMPLE 40

Synthesis of N-[N-phenylamino(phenylimino)methyl]-2-aminoethanoic acid

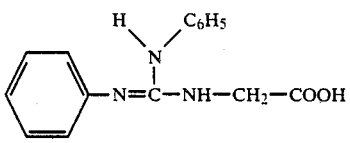

This compound is obtained from glycine and N,N'-diphenyl-S-methylisothiourea according to the experimental procedure described in Example 2 (yield 41%, melting point 214° C.).

The sweetening power of this compound corresponds approximately, on a weight basis, to 500 (five hundred) times that of a 2% sucrose solution.

EXAMPLE 41 synthesis of N-[N-phenylamino(4-cyanophenylimino)methyl]-2-aminoethanoic acid

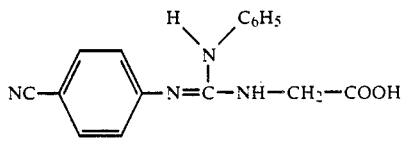

This compound is obtained from glycine and N-phenyl-N'-(4-cyanophenyl)-S-methylisothiourea according to the experimental procedure described in Example 2 (yield 33%; melting point 142° C.).

The sweetening power of this compound corresponds approximately, on a weight basis, to 4,000 (four thousand) times that of sucrose relative to a 2% sucrose solution, to 1,800 (one thousand eight hundred) times relative to a 5% sucrose solution and to 650 (six hundred and fifty) times relative to a 10% sucrose solution.

EXAMPLE 42

Synthesis of N-[N-cyclohexylamino(phenylimino)methyl]-2-aminoethanoic acid

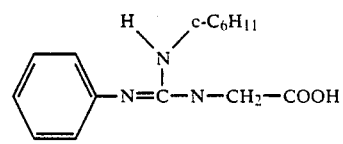

Step 1

Synthesis of N-cyclohexyl-N'-phenyl carbodiimide

A solution containing 2.0 g (8.55 mmol) of N-cyclohexyl-N'-phenylthiourea, 2.9 g (11.1 mmol) of triphenyl phosphine and 1.16 cm$^3$ (12 mmol) of carbon tetrachloride in 12 cm$^3$ of methylene chloride, is treated with 1.19 cm$^3$ (8.55 mmol) of triethylamine. The solution is heated for 2 hours, the precipitate which forms is eliminated by filtration and the filtrate is concentrated to dryness. The residue obtained is extracted with hexane and then filtered. The filtrates are then concentrated to dryness and 1.7 g (yield 100%) of the desired carbodiimide is obtained in the form of an oil.

Step 2

Synthesis of N-[N-cyclohexyl amino(phenylimino)methyl]-2-aminoethanoic acid

A suspension of 1.6 g (8 mmol) of the compound obtained previously and of 1.34 g (8 mmol) of glycine t-butyl ester hydrochloride in 20 cm$^3$ of acetonitrile is heated at reflux for 12 hours. The solution obtained is next concentrated to dryness in vacuo and the residual oil is triturated in ethyl ether. It is obtained in a solid form 2.7 g (yield 93%) of t-butyl N-[N-cyclohexylamino(phenylimino)methyl]-2-aminoethanoate.

A solution of 2 g (5.45 mmol) of the compound obtained previously in 8 cm$^3$ of acetic acid is stirred for one hour at 20° C. in the presence of 7.8 cm$^3$ (54.4 mmol) of 6.98M HCl in dioxane. After concentration to dryness in vacuo and trituration of the residue with ethyl ether, 1.6 g (yield 94%, melting point 160°–165°

C.) of the desired compound is obtained in the form of a hydrochloride.

The sweetening power of this compound corresponds approximately, on a weight basis, to 100 (one hundred) times that of a 2% sucrose solution.

EXAMPLE 43

Synthesis of N-[N-cyclohexylamino(4-cyanophenylimino)methyl]-2-aminoethanoic acid

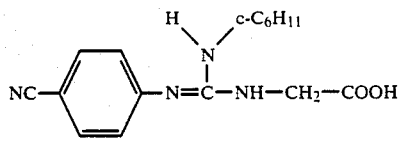

This compound is obtained from glycine and N-cyclohexyl-N'-(4-cyanophenyl)-S-methylisothiourea, according to the experimental procedure described in Example 2 (yield 58%; melting point 214° C.).

The sweetening power of this compound corresponds approximately, on a weight basis, to 12,000 (twelve thousand) times that of sucrose relative to a 2% sucrose solution, to 10,500 (ten thousand five hundred) times relative to a 5% sucrose solution and 8,500 (eight thousand five hundred) times relative to a 10% sucrose solution.

EXAMPLE 44

Synthesis of N-[N-cycloheptylamino(3,5-dichlorophenylimino)methyl]-2-aminoethanoic acid

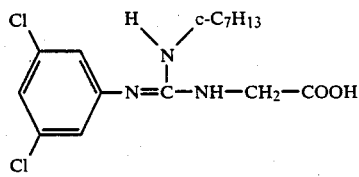

This compound is obtained from glycine and N-cycloheptyl-N'-(3,5-dichlorophenyl)-S-methylisothiourea according to the experimental procedure described in Example 2 (yield 87%; melting point 202° C.).

The sweetening power of this compound corresponds approximately, on a weight basis, to 20,000 (twenty thousand) times that of sucrose (compared with a 2% sucrose solution).

EXAMPLE 45

Synthesis of N-[N-cycloheptylamino(4-cyanophenylimino)methyl]-2-aminoethanoic acid

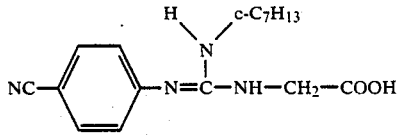

This compound is obtained from glycine and N-cycloheptyl-N'-(4-cyanophenyl)-S-methylisothiourea according to the experimental procedure described in Example 2 (yield 16%, melting point 220° C.).

The sweetening power of this compound corresponds approximately, on a weight basis, to 60,000 (sixty thousand) times that of a 2% sucrose solution.

EXAMPLE 46

Synthesis of N-[N-cyclooctylamino(3,5-dichlorophenylimino)methyl]-2-aminoethanoic acid

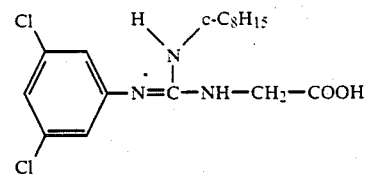

This compound is obtained from glycine and N-cyclooctyl-N'-(3,5-dichlorophenyl)-S-methylisothiourea according to the experimental procedure described in Example 2 (yield 61%; melting point 199° C.).

The sweetening power of this compound corresponds approximately, on a weight basis, to 60,000 (sixty thousand) times that of a 2% sucrose solution.

EXAMPLE 47

Synthesis of N-[N-cyclooctylamino(4-cyanophenylimino)methyl]-2-aminoethanoic acid

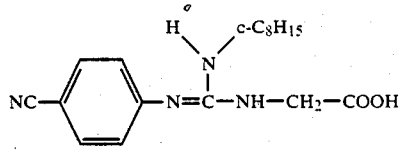

This compound is obtained from glycine and N-cyclooctyl-N'-(4-cyanophenyl)-S-methylisothiourea according to the experimental procedure described in Example 2 (yield 80%, melting point 228° C.).

The sodium or potassium salts of the compound may be obtained after dissolving 1 gram of the product in 3 cm$^3$ of 1N sodium hydroxide solution or 1N potassium hydroxide solution and concentrating to dryness.

The sweetening power of these compounds corresponds approximately, on a weight basis, to 170,000 (one hundred and seventy thousand) times that of a 2% sucrose solution, 130,000 (one hundred and thirty thousand) times relative to a 5% sucrose solution and 100,000 (one hundred thousand) times relative to a 10% sucrose solution.

EXAMPLE 48

Synthesis of N-[N-cyclooctylamino(4-cyano-3-methylphenylimino)methyl]-2-aminoethanoic acid

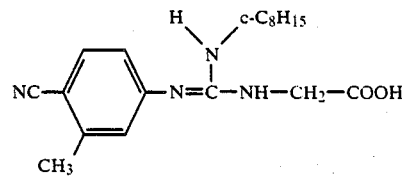

This compound is obtained from glycine and N-cyclooctyl-N'-(4-cyano-3-methylphenyl)-S-methylisothiourea following the experimental procedure described in Example 2 (yield 30%, melting point 155° C.).

The sweetening power of this compound corresponds approximately, on a weight basis, to 80,000 (eighty thousand) times that of a 2% sucrose solution.

EXAMPLE 49

Synthesis of
N-[N-cyclooctylamino(3-chloro-4-cyanophenylimino)-methyl]-2-aminoethanoic acid

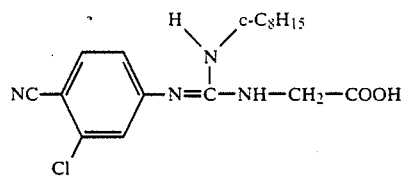

This compound is obtained from glycine and N-cyclooctyl-N'-(3-chloro-4-cyanophenyl)-S-methylisothiourea following the experimental procedure described in Example 2 (yield 68%, melting point 156° C.).

The sweetening power of this compound corresponds approximately, on a weight basis, to 100,000 (one hundred thousand) times that of a 2% sucrose solution.

EXAMPLE 50

Synthesis of
N-[N-cyclononylamino(4-cyanophenylimino)methyl]-2-aminoethanoic acid

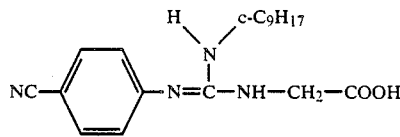

This compound is obtained from glycine and N-cyclononyl-N'-(4-cyanophenyl)-S-methylisothiourea following the experimental procedure described in Example 2 (yield 70%, melting point 195° C.).

The sweetening power of this compound corresponds approximately, on a weight basis, to 200,000 (two hundred thousand) times that of a 2% sucrose solution.

EXAMPLE 51

Synthesis of
N-[N-benzylamino(3,5-dichlorophenylimino)methyl]-2-aminoethanoic acid

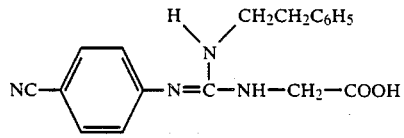

This compound is obtained from glycine and from N-phenylethyl-N'-(4-cyanophenyl)-S-methylisothiourea, following the experimental procedure described in Example 2 (yield 52%; melting point 129° C.).

The sweetening power of this compound corresponds approximately, on a weight basis, to 8,500 (eight thousand five hundred) times that of sucrose relative to a 2% sucrose solution, to 6,100 (six thousand one hundred) times relative to a 5% sucrose solution and to 4,200 (four thousand two hundred) times relative to a 10% sucrose solution.

EXAMPLE 54 synthesis of
N-[N-(R)-α-methylbenzylamino(4-cyanophenylimino)-methyl]-2-aminoethanoic acid

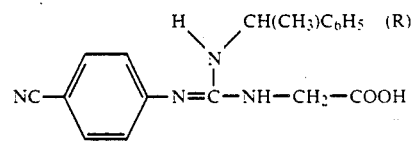

This compound is obtained from glycine and N-(R)-α-methylbenzyl-N'-(4-cyanophenyl)-S-methylisothiourea, following the experimental procedure described in Example 2 [yield 71%; $[\alpha]_D^{20} -112.5°$ (c=1, 0.5N HCl); melting point 189° C.].

The sweetening power of this compound corresponds approximately, on a weight basis, to 9,000 (nine thousand) times that of sucrose relative to a 2% sucrose solution, to 6,600 (six thousand six hundred) times relative to a 5% sucrose solution and to 2,500 (two thousand five hundred) times relative to a 10% sucrose solution.

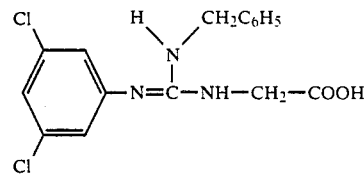

This compound is obtained from glycine and N-benzyl-N'-(3,5-dichlorophenyl)-S-methylisothiourea following the experimental procedure described in Example 2 (yield 35%, melting point 182° C.).

The sweetening power of this compound corresponds approximately, on a weight basis, to 80,000 (eighty thousand) times that of a 2% sucrose solution.

EXAMPLE 52

Synthesis of
N-[N-benzylamino(4-cyanophenylimino)methyl]-2-aminoethanoic acid

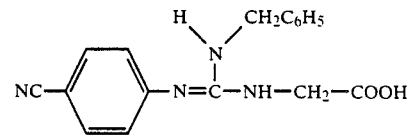

This compound is obtained from glycine and N-benzyl-N'-(4-cyanophenyl)-S-methylisothiourea following the experimental procedure described in Example 2 (yield 31%, melting point 149° C.).

The sweetening power of this compound corresponds approximately, on a weight basis, to 30,000 (thirty thousand) times that of sucrose when compared with a 2% sucrose solution, to 27,000 (twenty-seven thousand) times compared with a 5% sucrose solution, and 22,000 (twenty-two thousand) times compared with a 10% sucrose solution.

EXAMPLE 53

Synthesis of N-[N-phenylethylamino(4-cyanophenylimino)methyl]-2-aminoethanoic acid

EXAMPLE 55

Synthesis of N-[N-cyclohexylmethylamino(phenylimino)methyl]-2-aminoethanoic acid

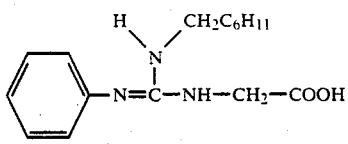

This compound is obtained from glycine and N-cyclohexylmethyl-N'-phenyl-S-methylisothiourea, following the experimental procedure described in Example 2 (yield 33%; melting point 185° C.).

The sweetening power of this compound corresponds approximately, on a weight basis, to 3,300 (three thousand three hundred) times that of sucrose relative to a 2% sucrose solution, to 2,500 (two thousand five hundred) times relative to a 5% sucrose solution and to 2,000 (two thousand) times relative to a 10% sucrose solution.

EXAMPLE 56

Synthesis of N-[N-cyclohexylmethylamino(3-cyanophenylimino)-methyl]-2-aminoethanoic acid

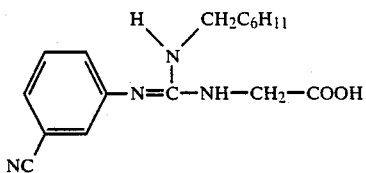

Step 1

Synthesis of N-(3-cyanophenyl)-N'-t-butyloxycarbonylmethylthiourea 2.8 cm³ (20 mmol) of triethylamine and 3.2 g (20 mmol) of 3-cyanophenyl isothiocyanate are added at 0° C. to a solution of 3.35 g (20 mmol) of glycine t-butyl ester in 150 cm³ of dichloromethane. The mixture is stirred at 20° C. for 12 hours before being concentrated under vacuum and then taken up with a mixture of water and ethyl ether (300:300). The ether phase is separated off and washed with a 1N hydrogen chloride solution (200 cm³), and then with a saturated sodium chloride solution. After drying with magnesium sulfate and concentration under vacuum, 5.17 g (89% yield) of a yellow solid is obtained, whose melting point is 131°–132° C.

Step 2

Synthesis of N-[N-cyclohexylmethylamino(3-cyanophenylimino)-methyl]-2-aminoethanoic acid 2.23 g (10.82 mmol) of dicyclohexylcarbodiimide and 1.4 cm³ (1.1 equivalent) of cyclohexylmethylamine are added to a solution of 3 g (10.3 mmol) of the above thiourea in 70 cm³ of ethyl acetate. The mixture is heated at reflux for 72 hours under nitrogen and is then concentrated down to 20 cm³. The solid obtained after cooling is removed by filtration, and the filtrate is concentrated under vacuum. The oil obtained is purified by chromatography on silica gel (eluent: 5:95 methanol-:ethyl acetate). 2.07g (54% yield) of a pale yellow oil is obtained. 0.4 g (1.08 mmol) of the t-butyl ester thus obtained is dissolved in 1.6 cm³ of pure acetic acid and is then treated by dropwise addition of 1.6 cm³ (10.81 mmol) of 6.82M hydrogen chloride in dioxane. After 2 hours at ambient temperature, the solution is concentrated under vacuum and the oil obtained is placed in contact with 100 cm³ of ethyl ether for 24 hours. After filtration, 0.31 g (82% yield, melting point 80°–83° C.) of the required compound is obtained in the form of hydrochloride.

The sweetening power of this compound corresponds approximately, on a weight basis, to 5,000 (five thousand) times that of a 2% sucrose solution.

EXAMPLE 57

Synthesis of N-[N-cyclohexylmethylamino(3,5-dichlorophenylimino)methyl]-2-aminoethanoic acid

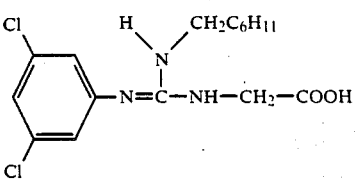

This compound is obtained from glycine and N-chclohixylmethyl-N'-(3,5-dichlorophenyl)-S-methylisothiourea according to the experimental procedure described in Example 2 (yield 50%; melting point 186° C.

The sweetening power of this compound corresponds approximately, on a weight basis, to 35,000 (thirty-five thousand) times that of a 2% sucrose solution.

EXAMPLE 58

Synthesis of N-[N-cyclohexylmethylamino(4-chlorophenylimino)-methyl]-2-aminoethanoic acid

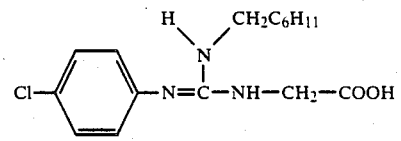

This compound is obtained from glycine and N-cyclohexylmethyl-N'-(4-chlorophenyl)-S-methylisothiourea, following the experimental procedure described in Example 2 (yield 33%; melting point 183° C.).

The sweetening power of this compound corresponds approximately, on a weight basis, to 3,500 (three thousand five hundred) times that of sucrose relative to a 2% sucrose solution, to 2,700 (two thousand seven hundred) times relative to a 5% sucrose solution and to 1,500 (one thousand five hundred) times when compared with a 10% sucrose solution.

EXAMPLE 59 synthesis of
N-[N-cyclohexylmethylamino(4-cyanophenylimino)-methyl]-2-aminoethanoic acid

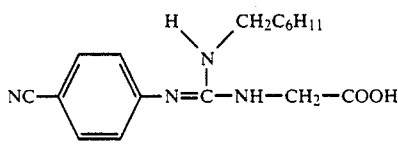

This compound is obtained from glycine and N-cyclohexylmethyl-N'-(4-cyanophenyl)-S-methylisothiourea, following the experimental procedure described in Example 2 (yield 48%; melting point 180° C.).

The sweetening power of this compound corresponds approximately, on a weight basis, to 35,000 (thirty-five thousand) times that of sucrose compared with a 2% sucrose solution, to 28,000 (twenty-eight thousand) times relative to a 5% sucrose solution, and to 17,000 (seventeen thousand) times relative to a 10% sucrose solution.

EXAMPLE 60

Synthesis of
N-[N-cyclohexylmethylamino(4-methoxycarbonylphenylimino)methyl]-2-aminoethanoic acid

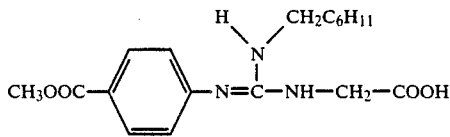

This compound is obtained from glycine and N-cyclohexylmethyl-N'-(4-methoxycarbonylphenyl)-S-methylisothiourea, following the experimental procedure described in Example 2 (yield 57%; melting point 182° C.).

The sweetening power of this compound corresponds approximately, on a weight basis, to 1,300 (one thousand three hundred) times that of sucrose relative to a 2% sucrose solution, to 900 (nine hundred) times relative to a 5% sucrose solution and to 500 (five hundred) times relative to a 10% sucrose solution.

EXAMPLE 61

Synthesis of
N-[N-cyclohexylmethylamino(4-carboxyphenylimino)-methyl]-2-aminoethanoic acid

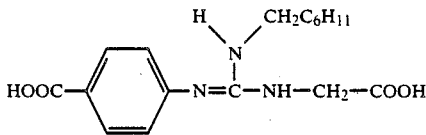

This compound is obtained (yield 79%; melting point 164° C.), by saponification of N-[N-cyclohexylmethylamino(4-caraboxyphenylimino)methyl]-2-aminoethanoic acid (melting point 163° C.) in a 1N sodium hydroxide solution, whereby the former was prepared from glycine and N-cyclohexylmethyl-N'-(4-methoxycarbonylphenyl)-S-methylisothiourea according to the experimental procedure described in Example 2.

The sweetening power of this compound corresponds approximately, on a weight basis, to 50 (fifty) times that of a 2% sucrose solution.

EXAMPLE 62

Synthesis of
N-[N-cyclohexylmethylamino(4-nitrophenylimino)methyl]-2-aminoethanoic acid

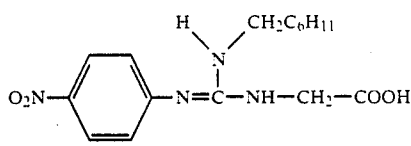

This compound is obtained from glycine and N-cyclohexylmethyl-N'-(4-nitrophenyl)-S-methylisothiourea, following the experimental procedure described in Example 2 (yield 39%; melting point 203° C.).

The sweetening power of this compound corresponds approximately, on a weight basis, to 8,000 (eight thousand) times that of sucrose relative to a 2% sucrose solution, to 7,500 (seven thousand five hundred) times relative to a 5% sucrose solution and to 4,000 (four thousand) times relative to a 10% sucrose solution.

EXAMPLE 63

Synthesis of
N-[N-(S)-1-cyclohexylethylamino(3,5-dichlorophenylimino)methyl]-2-aminoethanoic acid

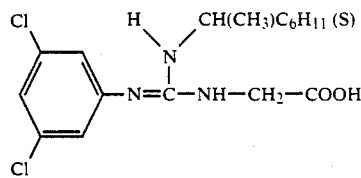

This compound is obtained from glycine and N-(S)-1-cyclohexylethyl-N'-(3,5-dichlorophenyl)-S-methylisothiourea according to the experimental procedure described in Example 2 (yield 80%; melting point 150° C.).

The sweetening power of this compound corresponds approximately, on a weight basis, to 70,000 (seventy thousand) times that of a 2% sucrose solution.

EXAMPLE 64

Synthesis of
N-[N-(2-methylphenyl)amino(4-cyanophenylimino)methyl]-2-aminoethanoic acid

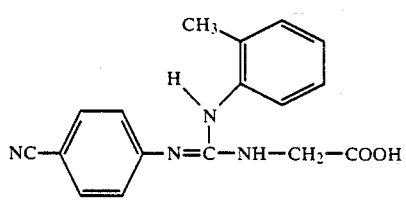

This compound is obtained from glycine and N-(2-methylphenyl)-N'-(4-cyanophenyl)-S-methylisothiourea following the experimental procedure described in Example 2 (yield 69%, melting point 165° C.).

The sweetening power of this compound corresponds approximately, on a weight basis, to 5,000 (five thousand) times that of a 2% sucrose solution.

EXAMPLE 65

Synthesis of N-[N-(3-methylphenyl)amino(4-cyanophenylimino)methyl]-2-aminoethanoic acid

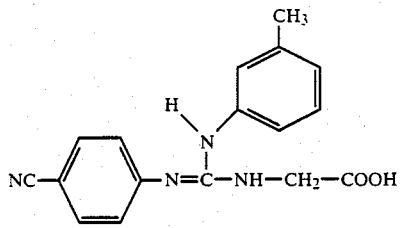

This compound is obtained from glycine and N-(3-methylphenyl)-N'-(4-cyanophenyl)-S-methylisothiourea according to the experimental procedure described in Example 2 (yield 69%, melting point 220° C.).

The sweetening power of this compound corresponds approximately, on a weight basis, to 9,000 (nine thousand) times that of a 2% sucrose solution.

EXAMPLE 66

Synthesis of N-[N-(4-methylphenyl)amino(4-cyanophenylimino)methyl]-2-aminoethanoic acid

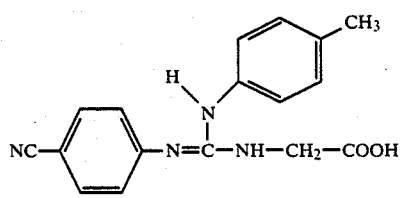

This compound is obtained from glycine and N-(4-methylphenyl)-N'-(4-cyanophenyl)-S-methylisothiourea according to the experimental procedure described in Example 2 (yield 45%, melting point 216° C.).

The sweetening power of this compound corresponds approximately, on a weight basis, to 7,000 (seven thousand) times that of a 2% sucrose solution.

EXAMPLE 67

Synthesis of N-[N-(1-methylcyclohexyl)amino(4-cyanophenylimino)methyl]-2-aminoethanoic acid

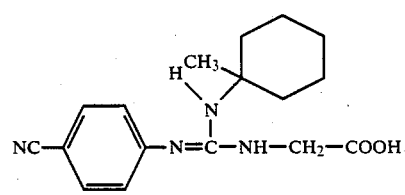

Step 1

Synthesis of N-(1-methylcyclohexyl)-N'-(4-cyanophenyl) thiourea

To a solution, chilled at 0° C., of 10.26 g (64.05 mmol) of 4-cyanophenyl isothiocyanate in 250 cm³ of ethyl acetate, is added, 7.59 g (67.1 mmol) of 1-methylcyclohexylamine. The solution is then stirred overnight at ambient temperature. The precipitate formed is filtered and then washed in ethyl ether. The filtrate is then concentrated to dryness in vacuo and the residue is triturated with ethyl ether (50 cm³) to obtain a second portion of thiourea. There was finally obtained 14.43 g (yield 82.5%) of the desired thiourea.

Step 2

Synthesis of N-[N-(1-methyl cyclohexyl)amino(4-cyanophenylimino)methyl]-2-aminoethanoic acid (HCl)

A suspension of 1.39 g (5.08 mmol) of N-(1-methylcyclohexyl)-N'-(4-cyanophenyl) thiourea, of 1 g (7.63 mmol) of glycine tert-butyl ester, of 1.57 g (7.63 mmol) of dicyclohexylcarbodiimide and of 0.05 cm³ (0.34 mmol) of triethylamine in 10 cm³ of ethyl acetate is stirred for four hours at ambient temperature. The dicyclohexylthiourea formed is removed by filtration and the filtrate is concentrated to dryness. The residue obtained is purified by chromatography (on a column of 50 mm of diameter and eluted with $CH_2Cl_2$—$CH_3OH$ 95–5/$CH_2Cl_2$ containing 0.6% of $NH_4OH$), and then recrystallized with hexane. 1.43 g (yield 76%) of tertbutyl N-[N-(1-methylcyclohexyl)amino(4-cyanophenylimino)methyl-2-aminoethanoate is obtained.

1.9 cm³ of a solution of 6.98N (13 mmol) HCl in dioxane and of 3.8 cm³ of acetic acid are mixed with 0.5 (1.35 mmol) of the compound previously obtained. The solution is stirred for 40 minutes and the reaction is quenched by the addition of 100 cm³ of ethyl ether, which promotes the formation of an oil which crystallizes after several hours of stirring. The solid is filtered off and is then washed with ethyl ether. After drying, 0.425 g (yield 90%) of the desired compound was obtained.

Step 3

Synthesis of N-[N-(1-methylcyclohexyl)amino(4-cyanophenylimino)methyl]-2-aminoethanoic acid A suspension of 0.508 g (1.45 mmol) of the hydrochloride previously obtained in a mixture of water-methanol (25–5), is mixed with 0.475 g (11.9 mmol) of sodium hydroxide. The mixture is filtered and the methanol is removed in vacuo. The solution is neutralized at pH 7 by addition of a 10% hydrogen chloride solution and afterwards is filtered after being stirred overnight. 0.31 g (yield 68%) of the desired product was obtained.

The sweetening power of this compound corresponds approximately, on a weight basis, to 100 (one hundred) times that of a 2% sucrose solution.

EXAMPLE 68

Synthesis of
N-[N-1-naphthylamino(3,5-dichlorophenylimino)methyl]-2-aminoethanoic acid

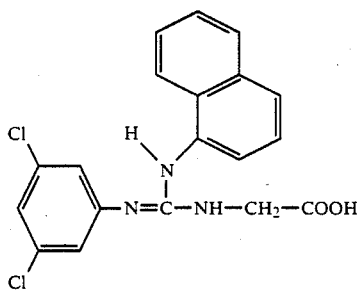

This compound is obtained from glycine and N-1-naphthyl-N'-(3,5-dichlorophenyl)-S-methylisothiourea according to the experimental procedure described in Example 2 (yield 78%; melting point 210° C.).

The sweetening power of this compound corresponds approximately, on a weight basis, to 30,00 (thirty thousand) times that of a 2% sucrose solution.

EXAMPLE 69

Synthesis of
N-[N-1-naphthylamino(4-cyanophenylimino)methyl]-2-aminoethanoic acid

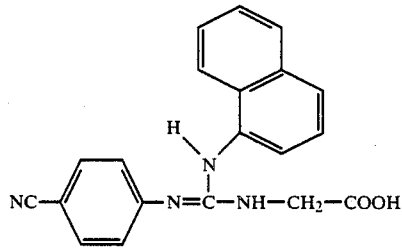

This compound is obtained from glycine and N-1-naphthyl-N'-(4-cyanophenyl)-S-methylisothiourea following the experimental procedure described in Example 2 (yield 44%; melting point 178° C.).

The sweetening power of this compound corresponds approximately, on a weight basis, to 60,000 (sixty thousand) times that of a 2% sucrose solution.

EXAMPLE 70

Synthesis of
N-[N-(1-indanyl)amino(4-cyanophenylimino)methyl]-2-aminoethanoic acid

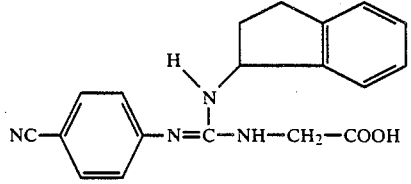

This compound is obtained from glycine and N-(1-indanyl)-N'-(4-cyanophenyl)-S-methylisothiourea according to the experimental procedure described in Example 2 (yield 62%, melting point 176° C.).

The sweetening power of this compound corresponds approximately, on a weight basis, to 5,000 (five thousand) times that of a 2% sucrose solution.

EXAMPLE 71

Synthesis of
N-[N-1-adamantyl)amino(4-cyanophenylimino)methyl]-2-aminoethanoic acid

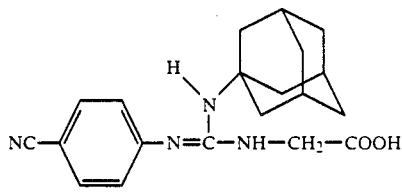

This compound is obtained from glycine and N-(1-adamantyl)-N'-(4-cyanophenyl)-S-methylisothiourea according to the experimental procedure described in Example 2 (yield 55%, melting point 232° C.).

The sweetening power of this compound corresponds approximately, on a weight basis, to 3,500 (three thousand five hundred) times that of a 2% sucrose solution.

EXAMPLE 72

Synthesis of
N-[N-(1-adamantylmethyl)amino(4-cyanophenylimino)methyl]-2-aminoethanoic acid

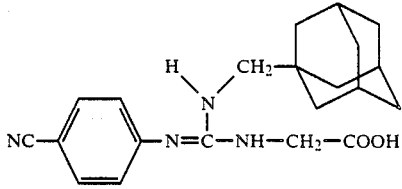

This compound is obtained from glycine and N-(1-adamantylmethyl)-N'-(4-cyanophenyl)-S-methylisothiourea according to the experimental procedure described in Example 2 (yield 62%, melting point 169° C.).

The sweetening power of this compound corresponds approximately, on a weight basis, to 23,000 (twenty three thousand) times that of a 2% sucrose solution.

EXAMPLE 73

Synthesis of N-[cyanoimino(3-chlorophenyl amino)methyl]-2-aminoethanoic acid

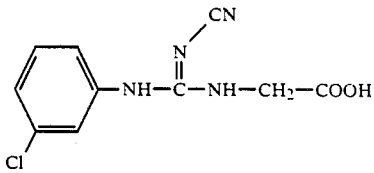

Ten grams (59 mmol) of 3-chlorophenyl isothiocyanate and 4.15 g (65 mmol) of monosodium cyanamide are mixed in 100 cm³ of absolute ethanol and kept boiling for 2 hours. After elimination of the solvent, the resulting solid residue is washed with 100 cm³ of ethyl ether. The compound is then suspended in a solution of 4.8 cm³ (77 mmol) of methyl iodide in 50 cm³ of ethanol. The mixture is then left at ambient temperature for 20 hours. The final precipitate is filtered and washed with water (2×50 cm³) and ethanol (2×50 cm³) and is then dried in vacuo. A 10.1 gram portion of N-(3-chlorophenyl)-N'-cyano-S-methylisothiourea is obtained with a melting point of 167° C.

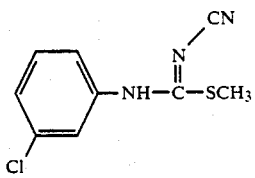

Three grams (39.9 mmol) of glycine and 1.5 g (37.2 mmol) of sodium hydroxide are mixed in 10 cm³ of water and added to 6 g (26.5 mmol) of N-(3-chlorophenyl)-N'-cyano-S-methylisothiourea in solution in 40 cm³ of 95% ethanol. The mixture is reflux heated for 1 hour. After cooling, the resulting precipitate is filtered and then washed with 2×50 cm³ of ethyl ether. The resulting solid is dissolved in 50 cm³ of 1N sodium hydroxide solution. This solution is washed with 3×10 cm³ of dichloromethane and then acidified with a 3N solution until a pH close to 2 is obtained. The white solid which forms is then filtered and washed in 2×10 cm³ of water, following which it is dried in vacuo. 6 g of N-[cyanoimino(3-clorophenylamino)methyl]-2-aminoethanoic acid (yield 89%) is obtained with a melting point of 109° C.

The sweetening power of this compound corresponds approximately, on a weight basis, to 80 (eighty) times that of a 2% sucrose solution.

EXAMPLE 74

Synthesis of N-[N-(N-methyl-N-phenylamino)(4-cyanophenylimino)methyl]-2-aminoethanoic acid

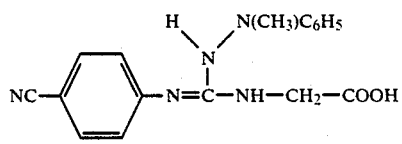

This compound is obtained from glycine and N-(N-methyl-N-phenylamino)-N'-(4-cyanophenyl)-S-methylisothiourea according to the experimental procedure described in Example 2 (yield 13%, melting point 202° C.).

The sweetening power of this compound corresponds approximately, on a weight basis, to 18,000 (eighteen thousand) times that of a 2% sucrose solution.

EXAMPLE 75

Synthesis of N-[N-(3,4-methylenedioxyphenyl) amino)4-cyanophenylimino)methyl]-2-aminoethanoic acid

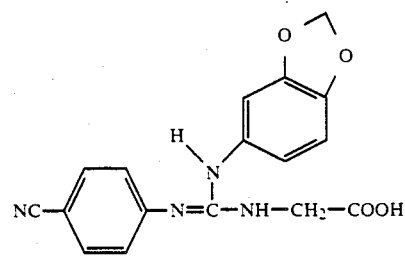

This compound is obtained from glycine and N-(3,4-methylenedioxyphenyl)-N'-(4-cyanophenyl)-S-methylisothiourea according to a the experimental procedure described in Example 2 (yield 10%, melting point 166° C.).

The sweetening power of this compound corresponds approximately, on a weight basis, to 5,000 (five thousand) times that of a 2% sucrose solution.

EXAMPLE 76

Synthesis of N-[N-morpholinoamino(3,5-dichlorophenylimino)methyl]-2-aminoethanoic acid

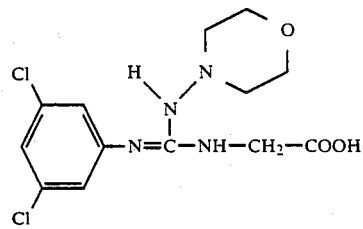

This compound is obtained from glycine and N-morpholino-N'-(3,5-dichlorophenyl)-S-methylisothiourea according to the experimental procedure described in Example 2 (yield 20%, melting point 215° C.).

The sweetening power of this compound corresponds approximately, on a weight basis, to 500 (five hundred) times that of a 2% sucrose solution.

EXAMPLE 77

Synthesis of N-[N-morpholinoamino(4-cyanophenylimino)methyl]-2-aminoethanoic acid

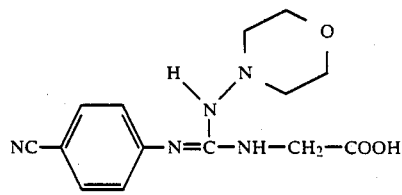

This compound is obtained from glycine and N-morpholino-N'-(4-cyanophenyl)-S-methylisothiourea according to the experimental procedure described in Example 2 (yield 11%, melting point 205° C.).

The sweetening power of this compound corresponds approximately, on a weight basis, to 950 (nine hundred and fifty) times that of a 2% sucrose solution.

EXAMPLE 78

Synthesis of N-[N-(2,2,4,4-tetramethylcyclobut-3-yl)amino(4-cyanophenylimino) methyl]-2-aminoethanoic acid

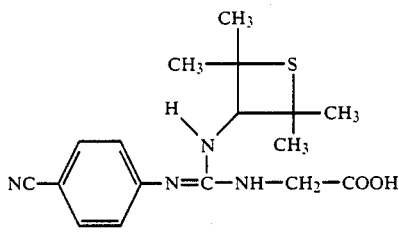

This compound is obtained from glycine and N-(2,2,4,4-tetramethylthiacyclobut-3-yl)-N'-(4-cyanophenyl)-S-methylisothiourea according to the experimental procedure described in Example 2 (yield 50%, melting point 237° C.).

The sweetening power of this compound corresponds approximately, on a weight basis, to 700 (seven hundred) times that of a 2% sucrose solution.

EXAMPLE 79 synthesis of N-]phenylsulfonylimino(phenylamino)methyl]-2-aminoethanoic acid

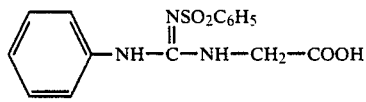

This compound is obtained from glycine and N-phenyl-N'-phenylsulfonyl-S-methylisothiourea, following the experimental procedure described in Example 80 (yield 10%, melting point 148° C.).

The sweetening potency of this compound corresponds approximately, on a weight basis, to 900 (nine hundred) times that of sucrose with respect to a 2% sucrose solution, to 800 (eight hundred) times with respect to a 5% sucrose solution and to 600 (six hundred) times with respect to a 10% sucrose solution.

EXAMPLE 80

Synthesis of N-[phenylsulfonylimino(3-chlorophenylamino)methyl]-2-aminoethanoic acid

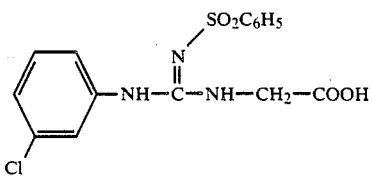

Six grams (35.4 mmol) of 3-chlorophenyl isothiocyanate and 6.1 g (38.9 mmol) of benzene sulfonamide are dissolved in 50 cm³ of acetone. A 1.55 gram portion (38.9 mmol) of sodium hydroxide is dissolved in 3 cm³ of water and the two solutions are mixed together. The mixture is maintained at ambient temperature for 2 hours. The precipitate which forms is filtered and washed with acetone and ethyl ether (2×20 cm³) and 11.3 g of a residue is obtained (yield 100%). This residue is dissolved in 50 cm³ of 95% ethanol containing 2.88 cm³ of methyl iodide (46 mmol). After 24 hours at ambient temperature, the solution is evaporated to dryness. The residue is next washed with ethyl ether (3×20 cm³) and then dried in vacuo. 8.75 g of N-(3-chlorophenyl)-N'-phenylsulfonyl-S-methylisothiourea is obtained with a melting point of 116° C.

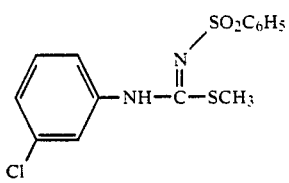

A 2.3 gram portion (30.7 mmol) of glycine, 1.15 g (28.6 mmol) of sodium hydroxide in 10 cm³ of water and 6.4 g (20.5 mmol) of N-(3-chlorophenyl)-N'-phenylsulfonyl-S-methylisothiourea are mixed in 50 cm³ of 95% ethanol. The mixture is heated at reflux for 9 hours. After concentration in vacuo, the residue obtained in this way is dissolved in 50 cm³ of a 1N sodium hydroxide solution. The solution is washed in dichloromethane (3×20 cm³) and in ethyl acetate (2×20 cm³) and then acidified by adding a 6N hydrogen chloride solution until a pH close to 3 is obtained.

After cooling, the precipitate which forms is filtered and washed with 2×5 cm³ of water, following which it is dried in vacuo. 5.6 g of N-[phenylsulfonylimino(3-chlorophenylamino)methyl]-2-aminoethanoic acid (yield 75%) is obtained with a melting point of 218° C.

The sweetening power of this compound corresponds approximately, on a weight basis, to 17,000 (seventeen thousand) times that of a 2% sucrose solution.

EXAMPLE 81

Synthesis of N-[phenylsulfonylimino(4-methylphenylamino)methyl]-2-aminoethanoic acid

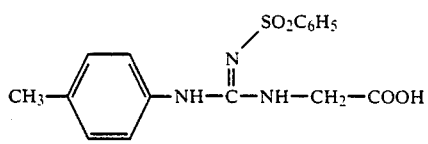

This compound is obtained from glycine and N-(4-methylphenyl)-N'-phenylsulfonyl-S-methylisothiourea following the experimental procedure described in Example 80 (yield 30%, melting point 220° C.).

The sweetening power of this compound corresponds approximately, on a weight basis, to 0.5 (one-half) times that of a 2% sucrose solution.

EXAMPLE 82

Synthesis of
N-[phenylsulfonylimino(4-chlorophenylamino)methyl]-2-aminoethanoic acid

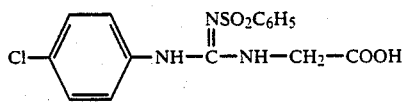

This compound is obtained from glycine and N-(4-chlorophenyl)-N'-phenylsulfonyl-S-methylisothiourea, following the experimental procedure described in Example 80 (yield 30%, melting point 133° C.).

The sweetening potency of this compound corresponds approximately, on a weight basis, to 2,000 (two thousand) times that of sucrose with respect to a 2% sucrose solution, to 1,400 (one thousand and four hundred) times with respect to a 5% sucrose solution, and to 750 (seven hundred and fifty) times with respect to a 10% sucrose solution.

EXAMPLE 83

Synthesis of
N-[phenylsulfonylimino(4-cyanophenylamino)methyl]-2-aminoethanoic acid

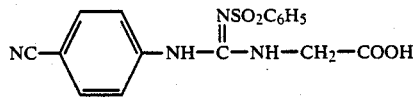

A mixture of 5 g (0.031 mol) of 4-cyanophenyl isothiocyanate and 6.3 g (0.04 mol) of benzenesulfonamide in 5 cm³ of acetone and also 1.6 g (0.04 mol) of sodium hydroxide in 3 cm³ of water is maintained for two hours at room temperature. The precipitate obtained is filtered and is then washed first with acetone (2×20 cm³) and then with ethyl ether (2×20 cm³). The final product (9 g; yield: 94%) is then placed in 50 cm³ of 95% ethanol containing 2.75 cm³ (0.044 mol) of methyl iodide. After 24 hours at room temperature the solution is concentrated to dryness and the residue is triturated with ethyl ether (3×30 cm³) and dried in vacuo. An 80% yield (8.5 g) of N-(4-cyanophenyl)-'-phenylsulfonyl-S-methylisothiourea (melting point 150° C.) is obtained:

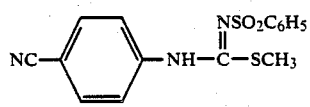

A mixture of 0.57 g (7.6 mmoles) of glycine and 0.3 g (7.6 mmoles) of sodium hydroxide in 3 cm³ of water and 2.5 (7.6 mmoles) of N-(4-cyanophenyl)-N'-phenylsulfonyl-S-methylisothiourea in 30 cm³ of 95% ethanol is heated to boiling for 7 hours. After cooling, the precipitate obtained is filtered and dissolved in 20 cm³ of 1N sodium hydroxide solution. The solution obtained is washed with dichloromethane (3×10 cm³) and ethyl acetate (2×10 cm³) and is then acidified to pH 3 with a 6N HCl solution. After cooling, precipitate forms and is filtered, washed with water (2×5 cm³) and dried in vacuo to give 1.4 g (yield 52%) of N-[phenylsulfonylimino(4-cyanophenylamino)methyl]-2-aminoethanoic acid having a melting point of 133° C.

The sweetening potency of this compound corresponds approximately, on a weight basis, to 45,000 (forty-five thousand) times that of sucrose with respect to a 2% sucrose solution, to 25,000 (twenty five thousand) times with respect to a 5% sucrose solution and to 15,000 (fifteen thousand) times with respect to a 10% sucrose solution.

EXAMPLE 84

Synthesis of
N-[phenylsulfonylimino(4-acetylphenylamino)methyl]-2-aminoethanoic acid

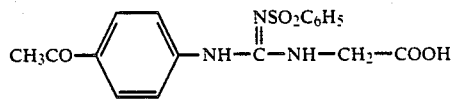

This compound is obtained from glycine and N-(4-acetylphenyl)-N'-phenylsulfonyl-S-methylisothiourea following the experimental procedure described in Example 80 (yield 38%, melting point 171° C.).

The sweetening potency of this compound corresponds approximately, on a weight basis, to 850 (eight hundred and fifty) times that of sucrose with respect to a 2% sucrose solution, to 750 (seven hundred and fifty) times with respect to a 5% sucrose solution, to 550 (five hundred and fifty) times with respect to a 10% sucrose solution.

EXAMPLE 85

Synthesis of
N-[phenylsulfonylimino(4-methylcarbamoylphenylamino)methyl]-2-aminoethanoic acid

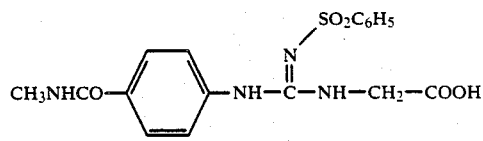

This compound is obtained from glycine and N-(4-methylcarbamoylphenyl)-N'-phenylsulfonyl-S-methylisothiourea following the experimental procedure described in Example 80 (yield 14%, melting point 130° C.).

The sweetening power of this compound corresponds approximately, on a weight basis, to 10 (ten) times that of sucrose (compared with a 2% sucrose solution).

EXAMPLE 86

Synthesis of
N-[benzylsulfonylimino(4-cyanophenylamino)methyl]-2-aminoethanoic acid

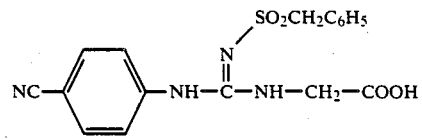

This compound is obtained from glycine and N-(4-cyanophenyl)-N'-benzylsulfonyl-S-methylisothiourea following the experimental procedure described in Example 80 (yield 53%, melting point 195° C.).

The sweetening power of this compound corresponds approximately, on a weight basis, to 20,000 (twenty thousand) times that of sucrose (compared with a 2% sucrose solution).

EXAMPLE 87

Synthesis of
N-[N-(3-chlorophenyl)amino((4-cyanophenylimino)-methyl]-2-aminoethanoic acid

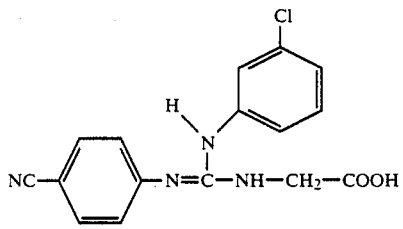

This compound is obtained from glycine and N-(3-chlorophenyl)-N'-(4-cyanophenyl)-S-methylisothiourea according to the experimental procedure described in Example 2 (yield 89%, melting point 198° C.).

The sweetening power of this compound corresponds approximately, on a weight basis, to 10,000 (ten thousand) times that of a 2% sucrose solution.

EXAMPLE 88

Synthesis of
N-[N-3,5-dichlorophenylamino(3,5-dichloro-phenylimino)methyl]-2-aminoethanoic acid

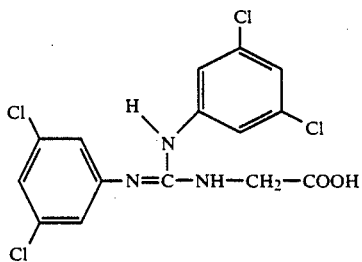

This compound is obtained from glycine and N,N'-bis(3,5-dichlorophenyl)-S-methylisothiourea according to the experimental procedure described in Example 2 (yield 35%; melting point 177° C.).

The sweetening power of this compound corresponds approximately, on a weight basis, to 1,000 (one thousand) times that of a 2% sucrose solution.

EXAMPLE 89

Synthesis of
N-[N,N-(tetramethylene)amino(4-cyanophenylimino)-methyl]-2-aminoethanoic acid

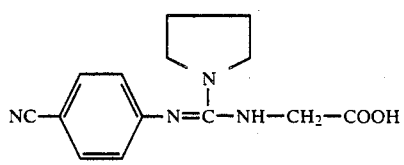

Step 1

Synthesis of
N-(4-cyanophenyl)-N'-t-butyloxycarbonylmethylthiourea 10.7 g (82 mmol) of glycine t-butyl ester are added to a solution of 13 g (82 mmol) of 4-cyanophenyl isothiocyanate dissolved in 100 cm³ of acetonitrile. After 12 hours of stirring, the precipitate formed is filtered off and is then washed with ethyl ether, to give 18.7 g (yield 78%) of the desired thiourea.

Step 2

Preparation of
N-4-cyanophenyl-N'-t-butyloxycarbonylmethyl-S-methylisothiourea

A mixture of 2.6 g (8.9 mmol) of the above thiourea and 1.6 g (11.4 mmol) of methyl iodide in 50 cm³ of acetone is stirred for 12 hours at 20° C. The mixture is concentrated to dryness and the residue is filtered off after trituration in ethyl ether. The hydroiodide obtained is dissolved in a 1N solution of sodium hydroxide and the mixture is extracted with dichloromethane. After drying over anhydrous sodium sulfate and concentration to dryness, 2.3 g (yield 82%) of the desired compound is obtained.

Step 3

Preparation of
N-[N,N-(tetramethylene)amino(4-cyanophenylimino)-methyl]-2-aminoethanoic acid in the form of hydrochloride The mixture of 6.5 g (21 mmol) of the above compound and 2.62 cm³ (31 mmol) of pyrrolidine in 100 cm³ of absolute ethanol is heated at 70° C. for 24 hours. 1.3 cm³ (15 mmol) of pyrrolidine is added again and heating is continued for 4 hours. The reaction mixture is concentrated to dryness under vacuum and the residue is purified by chromatography on a column of silica gel (eluent: 7:92.5:0.5 methanol:dichloromethane:ammonium hydroxide). 2.8 g (yield 40%) of the t-butyl ester of N-[N,N-(tetramethylene)-amino(4-cyanophenylimino)methyl]-2-aminoethanoic acid are obtained.

A solution of 1 g (3.13 mmol) of the above ester in 11 cm³ of acetic acid and 4.5 cm³ of a 6.98N HCl in dioxane are stirred for 1 hour.

The reaction mixture is poured into 1L of ethyl ether, the precipitate obtained is filtered off and dissolved in water and the solution obtained is lyophilized. 0.66 g (66% yield) of the required compound is obtained in the form of hydrochloride.

The sweetening power of this compound corresponds approximately, on a weight basis, to 100 (one hundred) times that of a 2% sucrose solution.

EXAMPLE 90

Synthesis of
N-[N,N-(pentamethylene)amino(4-cyanophenylimino)-methyl]-2-aminoethanoic acid

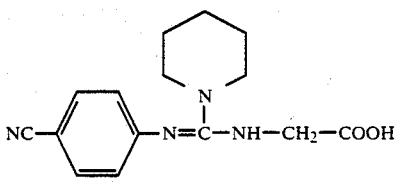

A mixture of 2.91 g (10 mmol) of N-(4-cyanophenyl)-N'-t-butyloxycarbonylmethylthiourea, 2.3 g (11 mmol) of dicylcohexylcarbodiimide dissolved in 50 cm³ of ethyl acetate, and 2 cm³ (20 mmol) of piperidine, is heated to 50° C. for 24 hours. After cooling, the dicyclohexylthiourea is removed and the filtrate is concentrated to dryness under vacuum, and 4 g of a red-colored oil is obtained. After purification on a silica gel column (7.5:92.5 methanol:dichloromethane), 1 g (yield 33%) of the t-butyl ester of N-[N,N-(pentamethylene)amino(4-cyanophenylimino)methyl]-2-aminoethanoic acid is obtained.

After removal of the t-butyl protective group according to the procedure described earlier, 0.71 g (yield 95%) of the required compound is obtained in the form of hydrochloride.

The sweetening power of this compound corresponds approximately, on a weight basis, to 200 (two hundred) times that of a 2% sucrose solution.

EXAMPLE 91

Synthesis of
N-[benzylimino(N-methyl-N-phenylamino)methyl]-2-aminoethanoic acid

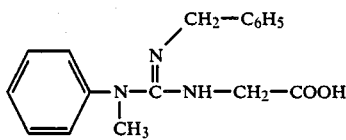

This compound is obtained from N-benzyl-N'-methyl-N'-phenyl-S-methylisothiourea following the experimental procedure described in Example 2 (yield 3%, melting point 138° C.).

The sweetening power of this compound corresponds approximately, on a weight basis, to 200 (two hundred) times that of a 2% sucrose solution.

EXAMPLE 92

Synthesis of
(R)-N-[N-cyclohexylamino(4-cyanophenylimino)methyl]-2-aminopropanoic acid

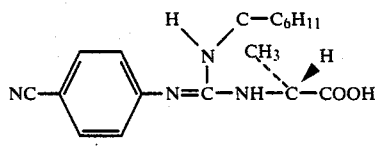

This compound is obtained from D-alanine and N-cyclohexyl-N'-(4-cyanophenyl)-S-methylisothiourea according to the experimental procedure described in Example 2 (yield 15%; melting point 177° C.).

The sweetening potency of this compound corresponds approximately, on a weight basis, to 100 (one hundred) times that of a 2% sucrose solution.

EXAMPLE 93

Synthesis of
(R)-N-[N-(S)-α-methylbenzylamino(3,5-dichlorophenylimino)methyl]-2-aminopropanoic acid

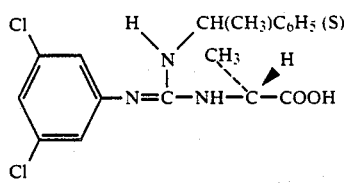

This compound is obtained from D-alanine and N-(S)-α-methylbenzyl-N'-(3,5-dichlorophenyl)-S-methylisothiourea according to the experimental procedure described in Example 2 (yield 77%; melting point 177° C.).

The sweetening potency of this compound corresponds approximately, on a weight basis, to 120 (one hundred and twenty) times that of a 2% sucrose solution.

EXAMPLE 94

Synthesis of
(R)-N-[N-cyclooctylamino(4-cyanophenylimino)methyl]-2-aminopropanoic acid

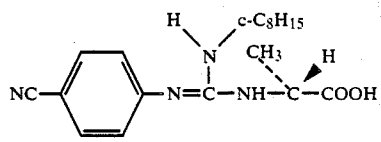

This compound is obtained from D-alanine and N-cyclooocytl-N'-(4-cyanophenyl)-S-methylisothiourea following the experimental procedure described in Example 2 (yield 70%, melting point 144° C.).

The sweetening power of this compound corresponds approximately, on a weight basis, to 900 (nine hundred) times that of a 2% sucrose solution.

EXAMPLE 95

Synthesis of
N-[N-methyl-N-benzylamino(3,5-dimethylphenylimino)]methyl-2-aminoethanoic acid

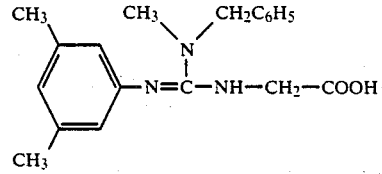

This compound is obtained from glycine and from N-methyl-N-benzyl-N'-(3,5-dimethylphenyl)-S-methylisothiourea following the experimental procedure described in Example 2 (yield 22%, melting point 141° C.).

The sweetening power of this compound corresponds approximately, on a weight basis, to 5,000 (five thousand) times that of a 2% sucrose solution.

EXAMPLE 96

Synthesis of N-[cyanoimino(4-cyanophenylamino)methyl]-2-aminoethanoic acid

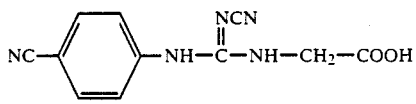

This compound is obtained from glycine and N-(4-cyanophenyl)-N'-cyano-S-methylisothiourea, following the experimental procedure described in Example 2 (yield 70%; melting point 103°–105° C., acetone-dichloromethane). Its sodium salt has a melting point of 178° C. (H$_2$O), its calcium salt, 184° C. (H$_2$O).

The sweetening potency of these compounds corresponds approximately, on a weight basis, to 7,000 (seven thousand) times that of sucrose with respect to a 2% sucrose solution, to 5,000 (five thousand) times with respect to a 5% sucrose solution, to 2,000 (two thousand) times with respect to a 10% sucrose solution.

EXAMPLE 97

Synthesis of N-[2,2-dicyano(4-cyanophenylamino)ethenyl]-2-aminoethanoic acid

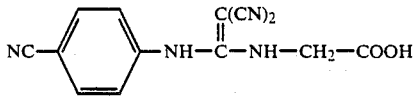

1,1-dicyano-2-(4-cyanophenylamino)-2-(methylthio)-ethene was produced according to the following procedure. A 2.88 gram portion of sodium hydride (in 50% dispersion in liquid paraffin), are added, in several fractions, to a solution, cooled to 0° C., of 3.96 g (0.06 mol) of malanonitrile dissolved in 30 cm$^3$ of dimethylformamide. The solution is then maintained for 10 minutes at 10° C. before the addition of 9.6 g (0.06 mol) of 4-cyanophenyl isothiocyanate dissolved in 20 cm$^3$ of dimethylformamide. The reaction mixture is maintained for 15 minutes at 20° C. then concentrated to dryness in vacuo. The residue obtained is triturated in boiling chloroform (5×50 cm$^3$) and the final solid obtained in dried in vacuo. 14 g of the solid thus obtained is then placed in contact for 2 hours at 20° C. with 7.8 g of dimethyl sulfate dissolved in 200 cm$^3$ of 95% ethanol. After elimination of ethanol and washing of the remaining solid by water (4×50 cm$^3$), 9.4 g (yield 70%) of 1,1-dicyano-2-(4-cyanophenylamino)-2-(methylthio)-ethene (melting point 160° C.) are obtained after drying.

Thereafter are mixed 10.5 g (0.14 mol) of glycine, 24 g (0.1 mol) of the compound obtained previously and 5.6 g (0.14 mol) of sodium hydroxide in a solution of 200 cm$^3$ of ethanol heated to boiling point. The reaction mixture is concentrated to dryness after 4 hours of contact and the residue obtained is dissolved in 200 cm$^3$ of a 2% aqueous sodium carbonate solution. The solution is washed with dichloromethane (3×50 cm$^3$) then acidified by a 3N HCl solution. The precipitate obtained is filtered and then washed with water (2×10 cm$^3$) (yield 50%; melting point 100° C., acetone-dichloromethane).

The sweetening potency of this compound corresponds approximately, on a weight basis, to 4,000 (four thousand) times that of sucrose with respect to a 2% sucrose solution, to 2,500 (two thousand five hundred) times with respect to a 5% sucrose solution, to 1,300 (one thousand three hundred) times with respect to a 10% sucrose solution.

EXAMPLE 98

Synthesis of N-[2-nitro(4-cyanophenylamino)ethenyl]-2-aminoethanoic acid

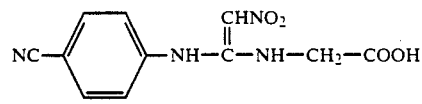

A mixture of 8.3 g (0.05 mol) of 1-nitro-2,2-(methylthio)-ethene and of 8.85 g (0.075 mol) of 4-aminobenzonitrile in 40 cm$^3$ of glacial acetic acid is heated at boiling point for 2 hours. After cooling, the precipitate obtained is filtered, washed with glacial acetic acid (5 cm$^3$), ethanol (2×10 cm$^3$), acetone (2×10 cm$^3$) and ethyl ether (2×10 cm$^3$). The resulting solid is recrystallized in dimethylsulfoxide. 3 g (yield 30%) of 1-nitro-2-(4-cyanophenylamino)-2-(methylthio)-ethene having a melting point of 188°–190° C. are obtained:

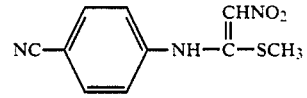

A mixture containing 0.15 g (2 mmol) of glycine, 0.41 g (2 mmol) of 1-nitro-2-(4-cyanophenylamino)-2-(methylthio)-ethene and 0.27 cm$^3$ (2 mmol) of triethylamine in 20 cm$^3$ of ethanol-water (5–1) is heated at boiling point for 3 hours. After concentration in vacuo, the residue obtained is dissolved in 20 cm$^3$ of 1N sodium hydroxide and the solution obtained is washed with ethyl acetate (4×10 cm$^3$) then acidified to a pH close to 3 with a 6N HCl solution. The white solid obtained is filtered, washed with water (2×2 cm$^3$) and dried in vacuo to produce 0.2 g (yield 38%) of N-[2-nitro(4-cyanophenylamino)ethenyl]-2-aminoethanoic acid having a melting point of 230° C.

The sweetening potency of this compound corresponds approximately, on a weight basis, to 9,000 (nine thousand) times that of sucrose with respect to a 2% sucrose solution, to 6,000 (six thousand) times with respect to a 5% sucrose solution, to 2,700 (two thousand seven hundred) times with respect to a 10% sucrose solution.

EXAMPLE 99

Synthesis of N-[methylsulfonylimino(4-cyanophenylamino)methyl]-2-aminoethanoic acid

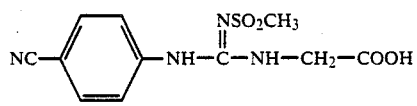

N-(4-cyanophenyl)-N'-methylsulfonyl-S-methylisothiourea was produced according to the following procedure.

A mixture of 5 g (0.31 mol) of 4-cyanophenyl isothiocyanate, of 3.8 g (0.04 mol) of methylsulfonamide in 50 cm³ of acetone and of 1.6 g (0.04 mol) of sodium hydroxide in 3 cm³ of water is maintained for two hours at room temperature. The precipitate obtained is filtered, washed with acetone and ethyl ether (2×20 cm³). The final solid is then placed in 50 cm³ of 95% ethanol containing 2.75 cm³ (0.044 mol) of methyl iodide. After 24 hours at room temperature, the solution is concentrated to dryness and the residue is washed with ethyl ether (3×20 cm³) and dried in vacuo to produce N-(4-cyanophenyl)-N'-methylsulfonyl-S-methylisothiourea.

A mixture of 0.57 g (7.6 mol) of glycine, of 0.3 g (7.6 mmol) of sodium hydroxide in 3 cm³ of water and of 2.0 g (7.6 mmol) of N-(4-cyanophenyl)-N'-methylsulfonyl-S-methylisothiourea in 30 cm³ of 95% ethanol is heated at boiling point for 7 hours. After cooling, the precipitate obtained is filtered and dissolved in 20 cm³ of a 1N sodium hydroxide solution. The solution obtained is washed with dichloromethane (3×10 cm³) and ethyl acetate (2×10 cm³) then acidified to a pH close to 3 with a 6N HCl solution. After cooling, the precipitate obtained is filtered, washed with water (2×5 cm³) and dried in vacuo to give N-[methylsulfonylimino(4-cyanophenylamino)methyl]-2-aminoethanoic acid (yield 55%) having a melting point of 170° C.

The sweetening potency of this compound corresponds approximately, on a weight basis, to 4,000 (four thousand) times that of sucrose with respect to a 2% sucrose solution, to 2,500 (two thousand and five hundred) times with respect to a 5% sucrose solution, to 1,400 (one thousand and four hundred) times with respect to a 10% sucrose solution.

Table I below lists the compounds synthesized in Examples 1 through 99 and presented along with their equivalent sweetening potencies as compared to a 2% sucrose solution as well as numerous other compounds organized according to structural similarity.

TABLE I

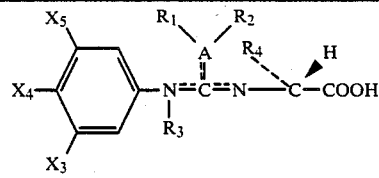

| Cpd. | X3 | X4 | X5 | A | R1 | R2 | R3 | R4 | Sweetness 2% |
|---|---|---|---|---|---|---|---|---|---|
| 1 | H | H | H | N | H | (S)CH(CH3)C6H6 | | H | 5,000 |
| 2 | Br | H | H | N | H | (S)CH(CH3)C6H5 | | H | 25,000 |
| 3 | CF3 | H | H | N | H | (S)CH(CH3)C6H5 | | H | 7,500 |
| 4 | CH3 | H | H | N | H | (S)CH(CH3)C6H5 | | H | 12,000 |
| 5 | C2H5 | H | H | N | H | (S)CH(CH3)C6H5 | | H | 4,500 |
| 6 | Cl | H | H | N | H | (S)CH(CH3)C6H5 | | H | 30,000 |
| 7 | CN | H | H | N | H | (S)CH(CH3)C6H5 | | H | 5,500 |
| 8 | NO2 | H | H | N | H | (S)CH(CH3)C6H5 | | H | 6,000 |
| 9 | OCH3 | H | H | N | H | (S)CH(CH3)C6H5 | | H | 4,500 |
| 10 | SCH3 | H | H | N | H | (S)CH(CH3)C6H5 | | H | 5,500 |
| 11 | H | CF3 | H | N | H | (S)CH(CH3)C6H5 | | H | 500 |
| 12 | H | CH3 | H | N | H | (S)CH(CH3)C6H5 | | H | 800 |
| 13 | H | Cl | H | N | H | (S)CH(CH3)C6H5 | | H | 3,000 |
| 14 | H | CN | H | N | H | (S)CH(CH3)C6H5 | | H | 28,000 |
| 15 | H | COCH3 | H | N | H | (S)CH(CH3)C6H5 | | H | 800 |
| 16 | H | COOCH3 | H | N | H | (S)CH(CH3)C6H5 | | H | 700 |
| 17 | H | F | H | N | H | (S)CH(CH3)C6H5 | | H | 4,000 |
| 18 | H | NO2 | H | N | H | (S)CH(CH3)C6H5 | | H | 7,000 |
| 19 | H | OCH3 | H | N | H | (S)CH(CH3)C6H5 | | H | 2,100 |
| 20 | H | OH | H | N | H | (S)CH(CH3)C6H5 | | H | 400 |
| 21 | H | SCH3 | H | N | H | (S)CH(CH3)C6H5 | | H | 1,200 |
| 22 | CH3 | CN | H | N | H | (S)CH(CH3)C6H5 | | H | 50,000 |
| 23 | Cl | Cl | H | N | H | (S)CH(CH3)C6H5 | | H | 17,000 |
| 24 | CF3 | H | OCH3 | N | H | (S)CH(CH3)C6H5 | | H | 7,000 |
| 25 | CH3 | H | CH3 | N | H | (S)CH(CH3)C6H5 | | H | 30,000 |
| 26 | Cl | H | Cl | N | H | (S)CH(CH3)C6H5 | | H | 120,000 |
| 27 | F | H | F | N | H | (S)CH(CH3)C6H5 | | H | 15,000 |
| 28 | Cl | Cl | Cl | N | H | (S)CH(CH3)C6H5 | | H | 35,000 |
| 29 | Cl | H | Cl | C | H | NO2 | H | H | 400 |
| 30 | Cl | H | CL | C | CN | CN | H | H | 30 |
| 31 | Cl | H | Cl | N | CH3 | CH2C6H5 | | H | 20,000 |
| 32 | H | CN | H | N | CH3 | CH(CH3)2 | | H | 80 |
| 33 | H | CN | H | N | CH3 | CH2C6H5 | | H | 3,000 |
| 34 | H | CN | H | N | C2H5 | CH2C6H5 | | H | 3,000 |
| 35 | H | CN | H | N | H | CH2CH3 | | H | 350 |
| 36 | H | CN | H | N | H | (CH2)5CH3 | | H | 6,000 |

TABLE I-continued

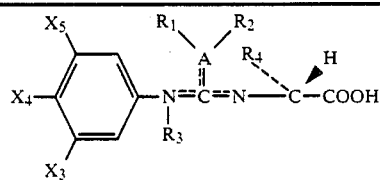

| Cpd. | X3 | X4 | X5 | A | R1 | R2 | R3 | R4 | Sweetness 2% |
|---|---|---|---|---|---|---|---|---|---|
| 37 | H | CN | H | N | H | (CH2)2CH(CH3)2 | | H | 200 |
| 38 | H | CN | H | N | H | C(CH3)2CH2CH3 | | H | 300 |
| 39 | H | CN | H | N | H | C(CH3)2CH2—C(CH3)3 | | H | 1.200 |
| 40 | H | H | H | N | H | C6H5 | | H | 500 |
| 41 | H | CN | H | N | H | C6H5 | | H | 4.000 |
| 42 | H | H | H | N | H | c-C6H11 | | H | 100 |
| 43 | H | CN | H | N | H | c-C6H11 | | H | 12.000 |
| 44 | Cl | H | Cl | N | H | c-C7H13 | | H | 20.000 |
| 45 | H | CN | H | N | H | c-C7H13 | | H | 60.000 |
| 46 | Cl | H | Cl | N | H | c-C8H15 | | H | 60.000 |
| 47 | H | CN | H | N | H | c-C8H15 | | H | 170.000 |
| 48 | CH3 | CN | H | N | H | c-C8H15 | | H | 80.000 |
| 49 | Cl | CN | H | N | H | c-C8H15 | | H | 100.000 |
| 50 | H | CN | H | N | H | c-C9H17 | | H | 200.000 |
| 51 | Cl | H | Cl | N | H | CH2C6H5 | | H | 80.000 |
| 52 | H | CN | H | N | H | CH2C6H5 | | H | 30.000 |
| 53 | H | CN | H | N | H | CH2CH2C6H5 | | H | 8.500 |
| 54 | H | CN | H | N | H | (R)CH(CH3)C6H5 | | H | 9.000 |
| 55 | H | H | H | N | H | CH2-c-C6H11 | | H | 3.300 |
| 56 | CN | H | H | N | H | CH2-c-C6H11 | | H | 5.000 |
| 57 | Cl | H | Cl | N | H | CH2-c-C6H11 | | H | 35.000 |
| 58 | H | Cl | H | N | H | CH2-c-C6H11 | | H | 3.500 |
| 59 | H | CN | H | N | H | CH2-c-C6H11 | | H | 35.000 |
| 60 | H | COOCH3 | H | N | H | CH2-c-C6H11 | | H | 1.300 |
| 61 | H | COOH | H | N | H | CH2-c-C6H11 | | H | 50 |
| 62 | H | NO2 | H | N | H | CH2-c-C6H11 | | H | 8.000 |
| 63 | Cl | H | Cl | N | H | (S)CH(CH3)-c-C6H11 | | H | 70.000 |
| 64 | H | CN | H | N | H | 2-CH3—C6H4 | | H | 5.000 |
| 65 | H | CN | H | N | H | 3-CH3—C6H4 | | H | 9.000 |
| 66 | H | CN | H | N | H | 4-CH3—C6H4 | | H | 7.000 |
| 67 | H | CN | H | N | H | 1-CH3-c-C6H10 | | H | 100 |
| 68 | Cl | H | Cl | N | H | 1-naphthyl | | H | 30.000 |
| 69 | H | CN | H | N | H | 1-naphthyl | | H | 60.000 |
| 70 | H | CN | H | N | H | 1-indanyl | | H | 5.000 |
| 71 | H | CN | H | N | H | 1-adamantyl | | H | 3.500 |
| 72 | H | CN | H | N | H | CH2-1-adamantyl | | H | 23.000 |
| 73 | Cl | H | H | N | | CN | H | H | 80 |
| 74 | H | CN | H | N | H | N(CH3)C6H5 | | H | 18.000 |
| 75 | H | CN | H | N | H | 3,4-CH2-dioxy-C6H3 | | H | 5.000 |
| 76 | Cl | H | Cl | N | H | morpholino | | H | 500 |
| 77 | H | CN | H | N | H | morpholino | | H | 950 |
| 78 | H | CN | H | N | H | 2,2,4,4-tetraCH3-thia-c-but-3-yl | | H | 700 |
| 79 | H | H | H | N | | SO2C6H5 | H | H | 900 |
| 80 | Cl | H | H | N | | SO2C6H5 | H | H | 17.000 |
| 81 | H | CH3 | H | N | | SO2C6H5 | H | H | <1 |
| 82 | H | Cl | H | N | | SO2C6H5 | H | H | 2.000 |
| 83 | H | CN | H | N | | SO2C6H5 | H | H | 45.000 |
| 84 | H | COCH3 | H | N | | SO2C6H5 | H | H | 850 |
| 85 | H | CONHCH3 | H | N | | SO2C6H5 | H | H | <10 |
| 86 | H | CN | H | N | | SO2CH2C6H5 | H | H | 20.000 |
| 87 | H | CN | H | N | H | 3-Cl-C6H4 | | H | 10.000 |
| 88 | Cl | H | Cl | N | H | 3,5-diCl-C6H3 | | H | 1.000 |
| 89 | H | CN | H | N | | CH2(CH2)2CH2 | | | 100 |
| 90 | H | CN | H | N | | CH2(CH2)3CH2 | | H | 200 |
| 91 | H | H | H | N | H | CH2C6H5 | CH3 | H | 200 |
| 92 | H | CN | H | N | H | c-C6H11 | | CH3 | 100 |
| 93 | Cl | H | Cl | N | H | (S)CH(CH3)C6H5 | | CH3 | 120 |
| 94 | H | CN | H | N | H | c-C8H15 | | CH3 | 900 |
| 95 | CH3 | H | CH3 | N | CH3 | CH2C6H5 | | H | 5.000 |
| 96 | H | CN | H | N | | CN | H | H | 7.000 |
| 97 | H | CN | H | N | CN | CN | H | H | 4.000 |
| 98 | H | CN | H | C | H | NO2 | | H | 9.000 |
| 99 | H | CN | H | N | | SO2CH3 | H | H | 4.000 |
| 100 | H | CN | H | N | CH3 | SO2C6H5 | | H | n.m. |
| 101 | H | CN | H | N | CH3 | c-C8H15 | | H | n.m. |
| 102 | H | CN | H | N | CH3 | c-C9H17 | | H | n.m. |
| 103 | CH3 | CN | H | N | CH3 | CH2C6H5 | | H | n.m. |
| 104 | CF3 | CN | CF3 | N | CH3 | CH2C6H5 | | H | n.m. |
| 105 | CH3 | CN | CH3 | N | H | (S)CH(CH3)C6H5 | | H | n.m. |

TABLE I-continued

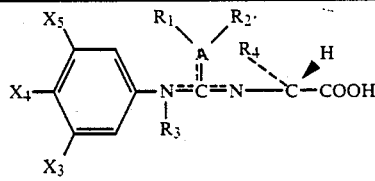

| Cpd. | X₃ | X₄ | X₅ | A | R₁ | R₂ | R₃ | R₄ | Sweetness 2% |
|------|-----|-----|-----|---|-----|--------------------------------|-----|----|------|
| 106 | CH₃ | CN | CH₃ | N | CH₃ | CH₂C₆H₅ | | H | n.m. |
| 107 | Cl | CN | Cl | N | CH₃ | CH₂C₆H₅ | | H | n.m. | n.m. = not made.

Table II below groups together those compounds which have been found to lack sweetness and/or produce a bitter taste in taste tests.

TABLE II

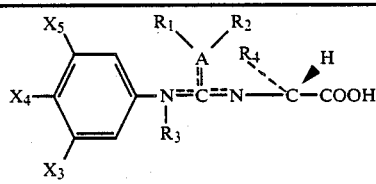

| Cpd. | X₃ | X₄ | X₅ | A | R₁ | R₂ | R₃ | R₄ | Taste |
|------|-----|----------|-----|---|-----------|-----------------------|-------|----------------|-------|
| 108 | CH₃ | H | H | N | | CH₂C₆H₅ | CH₃ | H | Bitter |
| 109 | CH₃ | H | H | N | | CH₂C₆H₅ | C₂H₅ | H | 0 |
| 110 | H | CN | H | N | | 4-CN—C₆H₄ | H | H | 0 |
| 111 | Cl | H | Cl | N | | fused-1-indanyl | H | H | Bitter |
| 112 | CN | H | H | N | H | (S)CH(CH₃)C₆H₅ | | CH₃ (D,L) | 0 |
| 113 | H | SO₂NHCH₃ | H | N | | SO₂C₆H₅ | H | H | 0 |
| 114 | H | CN | H | N | H | 1-CH₃-c-C₆H₁₀ | | CH₃ | 0 |
| 115 | H | CN | H | N | (CH₂)₃CH₃ | (CH₂)₃CH₃ | | H | Bitter |
| 116 | H | CN | H | N | CH₂CH=CH₂ | CH₂CH=CH₂ | | H | Bitter/Sweet |

It has been discovered that increased thermal stability is exhibited by those sweetening agents of the invention wherein R₁ is CH₃ instead of a hydrogen atom. As an illustration, the stability of three sweetening agents according to the invention were evaluated at pH 3 is a 1 mM phosphate buffer at 70° C. The concentration of unaffected sweetener was determined by HPLC. After 6 days under these conditions, only 50% of the sweetening agent of Example 14 (X₄=CN; X₃, X₅, R₁, R₃, R₄=H; A=N and R₂=(S)CH(CH₃)C₆H₅ remained unchanged. By contrast, after 7 days under the same conditions, 88% of the sweetening agent of Example 31 (X₃, X₅=Cl; X₄, R₃, R₄=H; A=N; R₁=CH₃ and R₂=CH₂C₆₅) remained unchanged. Similarly, 86% of the sweetening agent of Example 33 remained unchanged after 7 days (X₄=CN; X₃, X₅, R₃, R₄=H; A=N; R₁=CH₃ and R₂=CH₂C₆H₅).

It is further contemplated that sweetening agents according to the invention wherein R₃ is selected from the group consisting of C₁-C₃ alkyl will have improved stability properties. It is believed that the presence of a moiety other than H at the R₃ position sterically hinders cyclization of the molecule and thus prevents inactivation of the sweetening potential of the molecule.

Numerous sweetening agents and sweetening compositions are contemplated according to the present invention and it is not intended that the invention be limited to the specific embodiments illustrated herein. Consequently, only such limitations should be placed upon the invention as appear in the following claims.

What is claimed is:

1. A sweetening agent having the formula,

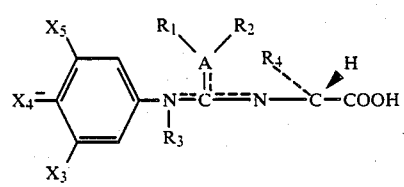

including tautomeric forms thereof and physiologically acceptable salts thereof;
wherein X₃, X₄ and X₅ are the same or different and are selected from the group consisting of
H,
Br,
CF₃,
CF₂CH₃,
CH₂CF₃,
C₁-C₄ alkyl,
CH=NOC₃,
CH=NOH,
CHO,
CH₂OCH₃,
CH₂OH,
Cl,
CN,
COCF₃,
COC₁-C₃ alkyl, CONH$_2$,
CONHC$_1$-C$_3$ alkyl,
CN(C$_1$-C$_3$ alkyl)$_2$,
COOC$_1$-C$_3$ alkyl,
COOH,
F,
I,
NH$_2$,
NHC$_1$-C$_3$ alkyl,
N(C$_1$-C$_3$ alkyl)$_2$,
NHCHO,
NHCOCH$_3$,
NHCONH$_2$,
NHSO$_2$CH$_3$,
NO$_2$,
OC$_1$C$_3$ alkyl,
OCOCH$_3$,
OH,
SC$_1$-C$_3$ alkyl,
SOC$_1$-C$_3$ alkyl,
SO$_2$C$_1$-C$_3$ alkyl,
SO$_2$NH$_2$,
SO$_2$NHC$_1$-C$_3$ alkyl,
SO$_2$N(C$_1$-C$_3$ alkyl)$_2$, and
SO$_3$H;
wherein A is selected from the group consisting of N and C;
wherein R$_1$ is an atom of hydrogen or R$_1$ is a C$_1$ to C$_4$ saturated, unsaturated, acyclic, cyclic or mixed hydrocarbyl or modified hydrocarbyl group and wherein, in the modified hydrocarbyl group,
  1 to 2 atoms of carbon may be replaced by 1 to 2 of the same or different heteroatoms selected from the group consisting of N, O, S, Cl, Br and I,
  and 1 to 3 atoms of hydrogen may be replaced by 1 to 3 atoms of fluorine;
wherein R$_2$ is a C$_2$ to C$_{13}$ saturated, unsaturated, acyclic, cyclic or mixed hydrocarbyl or modified hydrocarbyl group and wherein, in the modified hydrocarbyl group,
  1 to 4 atoms of carbon may be replaced by 1 to 4 of the same or different heteroatoms selected from the group consisting of N, O, S, Cl, Br and I,
  and 1 to 5 atoms of hydrogen may be replaced by 1 to 5 atoms of fluorine;
wherein R$_1$ and R$_2$ are different unless fused as a single moiety;
wherein R$_3$ is selected from the group consisting of H and C$_1$-C$_3$ alkyl; and
wherein R$_4$ is selected from the group consisting of H and CH$_3$;
with the proviso that, when X$_3$, X$_5$, R$_3$ and R$_4$ are atoms of hydrogen,
  and when X$_4$ is CN or NO$_2$, that R$_1$ and R$_2$ are not CN or OCH$_3$;
  and when X$_4$ is H, Cl, CN, COCH$_3$, F or NO$_2$, that R$_1$ is not NO$_2$, and that R$_2$ is not NO$_2$ or SO$_2$R, R being an alkyl, cycloalkyl, or aryl group having up to 10 atoms of carbon, or such a group wherein 1 or 2 carbon atoms are substituted by 1 or 2 atoms of sulfur or oxygen.

2. A sweetening agent according to claim 1 wherein A is N.

3. A sweetening agent according to claim 1 wherein R$_4$ is H.

4. A sweetening agent according to claim 1 wherein R$_3$ is selected from the group consisting of H and CH$_3$.

5. A sweetening agent according to claim 1 wherein R$_1$ is selected from the group consisting of H and CH$_3$.

6. A sweetening agent according to claim 1, 2, 3, 4 or 5 wherein X$_3$ and X$_5$ are selected from the group consisting of
H,
Br,
CF$_3$,
CH$_3$,
Cl and
F.

7. A sweetening agent according to claim 1, 2, 3, 4 or 5 wherein X$_4$ is selected from the group consisting of
H,
CN,
COOCH$_3$,
F and
NO$_2$.

8. A sweetening agent according to claim 1, 2, 3, 4 or 5 wherein R$_2$ is selected from the group consisting of
Normal alk(en)(yn)yl C$_2$-C$_{13}$,
Branched alk(en)(yn)yl C$_3$-C$_{13}$,
Cycloalk(en)yl C$_3$-C$_{13}$,
Alk(en)yl cycloalk(en)yl C$_4$-C$_{13}$,
Cycloalk(en)yl alk(en)yl C$_4$-C$_{13}$,
Alk(en)yl cycloalk(en)yl alk(en)yl C$_5$-C$_{13}$,
Alk(en)yl bicycloalk(en)yl C$_7$-C$_{13}$,
Fused bicycloalk(en)yl C$_7$-C$_{13}$,
Alk(en)yl fused bicycloalk(en)yl C$_8$-C$_{13}$,
Fused bicycloalk(en)yl alk(en)yl C$_8$-C$_{13}$,
Alkenyl fused bicycloalk(en)yl alk(en)yl C$_9$-C$_{13}$,
Fused tricycloalk(en)yl C$_{10}$-C$_{13}$,
Alk(en)yl fused tricycloalk(en)yl C$_{11}$-C$_{13}$,
Fused tricycloalk(en)yl alk(en)yl C$_{11}$-C$_{13}$ and
Alk(en)yl fused tricycloalk(en)yl alk(en)yl C$_{13}$.

9. A sweetening agent according to claim 8 wherein R$_2$ is selected from the group consisting of
n-C$_5$H$_{11}$, n-C$_6$H$_{13}$, n-C$_7$H$_{15}$,
CH(CH$_3$)(CH$_2$)$_2$CH$_3$,   CH(CH$_3$)(CH$_2$)$_3$CH$_3$,
(CH$_2$)$_3$CH(CH$_3$)$_2$,   (CH$_2$)$_4$CH(CH$_3$)$_2$,
(CH$_2$)$_5$CH(CH$_3$)$_2$,
C$_{65}$, C$_6$-C$_{10}$ cycloalkyl,
CH$_2$C$_{65}$, CH$_2$-c-C$_6$H$_{11}$, CH(CH$_3$)C$_6$H$_5$, CH(CH$_3$)-c-C$_{611}$,   (CH$_2$)$_2$C$_6$H$_5$,   (CH$_2$)$_2$-c-C$_6$H$_{11}$,
CH(CH$_3$)CH$_2$C$_6$H$_5$, CH(CH$_3$)CH$_2$-c-C$_6$H$_{11}$,
C$_6$H$_4$(CH$_3$), C$_6$-C$_{10}$ cycloalkyl(CH$_3$),
CH$_2$C$_6$H$_4$(CH$_3$),   CH$_2$-c-C$_6$H$_{10}$(CH$_3$)C$_6$H$_4$(CH$_3$),
CH(CH$_3$)-c-C$_6$H$_{10}$(CH$_3$),
(CH$_2$)$_2$CH(c-C$_3$H$_5$)$_2$,   (CH$_2$)$_3$CH(c-C$_3$H$_5$)$_2$,
CH(CH$_3$)CH$_2$CH(c-C$_3$H$_5$)$_2$,
CH(CH$_3$)(CH$_2$)$_2$CH(c-C$_3$H$_5$)$_2$,
naphthyl, 5,6,7,8-tetrahydronaphthyl, perhydronaphthyl, indenyl, indanyl,
naphthyl(CH$_3$),   5,6,7,8-tetrahydronaphthyl(CH$_3$), perhydronaphthyl(CH$_3$),   indenyl(CH$_3$),   indanyl(CH$_3$), fenchyl,
CH$_2$-naphthyl,   CH$_2$-5,6,7,8-tetrahydronaphthyl, CH$_2$-perhydronaphthyl, CH$_2$-indenyl, CH$_2$-indanyl,
CH$_2$-naphthyl(CH$_3$),   CH$_2$-5,6,7,8-tetrahydronaphthyl(CH$_3$), CH$_2$-perhydronaphthyl(CH$_3$), CH$_2$-indenyl(CH$_3$), CH$_2$-indanyl(CH$_3$),
adamantyl,
CH$_2$-adamantyl, CH(CH$_3$)adamantyl, and
CH$_2$-adamantyl(CH$_3$).

10. A sweetening agent according to claim 1, 2, 3, 4 or 5 wherein R$_2$ is a modified hydrocarbyl group wherein up to four carbon atoms may be replaced by the same or different heteroatoms selected from a group consisting of
S to replace C or $CH_2$,
N to replace CH or $CH_3$,
NH and O to replace $CH_2$ and
Cl, Br and I to replace $CH_3$, wherein up to 5 atoms of hydrogen may be substituted by fluorine atoms.

11. A sweetening agent according to claim 10 wherein $R_2$ is selected from the group consisting of
$N(CH_3)C_6H_5$, pyridinyl, piperidyl, homopiperidyl, indolyl, indolinyl, isoindolinyl, quinolyl, isoquinolyl, pyrazinyl, pyrimidyl, indazolyl, quinoxalinyl, quinazolinyl, purinyl,
$OCH_2C_6H_5$, pyranyl, benzofuranyl, methoxyphenyl, methyloxycarbonylphenyl, 3,4-methylenedioxyphenyl, morpholinyl, benzoxazolyl, acetamidophenyl, cyano, nitro,
thiophenyl, benzothiophenyl, 2,2,4,4-tetramethyl-thiacyclobut-3-yl, thiazolyl, isothiazolyl, $SO_2C_6H_5$, $SO_2C_6H_{11}$, $SO_2C_7H_{13}$,
chlorophenyl,
fluorophenyl and
trifluoromethylphenyl.

12. A sweetening agent according to claim 1 having the formula

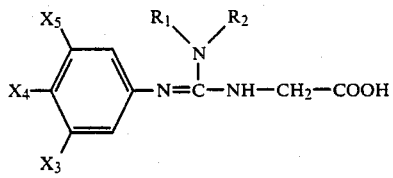

13. A sweetening agent according to claim 12 wherein $R_1$ is H.
14. A sweetening agent according to claim 12 wherein $R_1$ is $CH_3$.
15. A sweetening agent according to claim 12 wherein $X_3$ and $X_5$ are H and $X_4$ is CN.
16. A sweetening agent according to claim 12 wherein $X_3$ and $X_5$ are selected from the group consisting of $CF_3$, $CH_3$, Cl and F and wherein $X_4$ is selected from the group consisting of H and CN.
17. A sweetening agent according to claim 12 wherein $R_2$ is selected from the group consisting of $CH(CH_3)C_6H_5$, $CH_2C_6H_5$, $CH(CH_3)$-c-$C_6H_{11}$, c-$C_6H_{11}$, c-$C_7H_{13}$, c-$C_8H_{15}$, c-$C_9H_{17}$, c-$C_{10}H_{19}$, $SO_2C_6H_5$ and $SO_2C_7H_{13}$.
18. A sweetening agent according to claim 12 wherein $R_1$ is selected from the group consisting of H and $CH_3$, wherein $X_3$ and $X_5$ are H and $X_4$ is CN or wherein $X_3$ and $X_5$ are selected from the group consisting of $CF_3$, $CH_3$, Cl, H and F and wherein $X_4$ is selected from the group consisting of H and CN; and wherein $R_2$ is selected from the group consisting of $CH(CH_3)C_6H_5$, $CH_2C_6H_5$, $CH(CH_3)$-c-$C_6H_{11}$, c-$C_6H_{11}$, c-$C_7H_{13}$, c-$C_8H_{15}$, c-$C_9H_{17}$, c-$C_{1019}$, $SO_2C_6H_5$ and $SO_2C_7H_{13}$.
19. The sweetening agent according to claim 18 wherein $R_1$, $X_3$ and $X_5$ are H, $X_4$ is CN and $R_2$ is c-$C_9H_{17}$, including tautomeric forms thereof and physiologically acceptable salts thereof.
20. The sweetening agent according to claim 18 wherein $R_1$, $X_3$ and $X_5$ are H, $X_4$ is CN and $R_2$ is c-$C_8H_{15}$, including tautomeric forms thereof and physiologically acceptable salts thereof.
21. The sweetening agent according to claim 18 wherein $R_1$ and $X_4$ are H, $X_3$ and $X_5$ are Cl and $R_2$ is (S)CH($CH_3$)$C_6H_5$, including tautomeric forms thereof and physiologically acceptable salts thereof.
22. The sweetening agent according to claim 18 wherein $R_1$ and $X_5$ are H, $X_3$ is Cl, $X_4$ is CN and $R_2$ is c-$C_8H_{15}$, including tautomeric forms thereof and physiologically acceptable salts thereof.
23. The sweetening agent according to claim 18 wherein $R_2$ and $X_5$ are H, $X_3$ is $CH_3$, $X_4$ is CN and $R_2$ is c-$C_8H_{15}$, including tautomeric forms thereof and physiologically acceptable salts thereof.
24. The sweetening agent according to claim 18 wherein $R_1$ and $X_4$ are H, $X_3$ and $X_5$ are Cl and $R_2$ is $CH_2C_6H_5$, including tautomeric forms thereof and physiologically acceptable salts thereof.
25. The sweetening agent according to claim 18 wherein $R_1$ is $CH_3$, $X_4$ is H, $X_3$ and $X_5$ are Cl and $R_2$ is $CH_2C_6H_5$, including tautomeric forms thereof and physiologically acceptable salts thereof.
26. The sweetening agent according to claim 18 wherein $R_1$ and $X_4$ are H, $X_3$ and $X_5$ are Cl and $R_2$ is (S)CH($CH_3$)-c-$C_6H_{11}$, including tautomeric forms thereof and physiologically acceptable salts thereof.
27. The sweetening agent according to claim 18 wherein $R_1$, $X_3$ and $X_5$ are H, $X_4$ is CN and $R_2$ is (S)CH($CH_3$)$C_6H_5$, including tautomeric forms thereof and physiologically acceptable salts thereof.
28. The sweetening agent according to claim 18 wherein $R_1$ and $X_4$ are H, $X_3$ and $X_5$ are Cl and $R_2$ is c-$C_7H_{13}$, including tautomeric forms thereof and physiologically acceptable salts thereof.
29. A sweetening agent according to claim 1 wherein the agent is selected from the group of physiologically acceptable salts consisting of hydrochloride, sodium, potassium, ammonium, calcium and magnesium salts.
30. A sweetening agent having the formula,

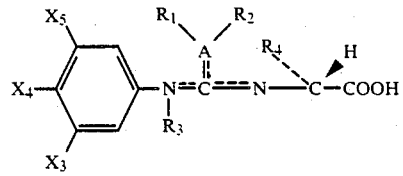

including tautomeric forms thereof and physiologically acceptable salts thereof;
wherein $X_3$, $X_4$ and $X_5$ are the same or different and are selected from the group consisting of
H,
Br,
$CF_3$,
$CF_2CF_3$,
$CH_2CF_3$,
$C_1$-$C_4$ alkyl
CH=$NOCH_3$,
CH=NOH,
CHO,
$CH_2OCH_3$,
$CH_2OH$,
Cl,
CN,
$COCF_3$,
$COC_1$-$C_3$ alkyl,
$CONH_2$,
$CONHC_1$-$C_3$ alkyl,
$CON(C_1$-$C_3$ alkyl$)_2$,
$COOC_1$-$C_3$ alkyl, COOH,
F,
I,
NH$_2$,
NHC$_1$-C$_3$ alkyl,
N(C$_1$-C$_3$ alkyl)$_2$,
NHCHO,
NHCOCH$_3$,
NHCONH$_2$,
NHSO$_2$CH$_3$,
NO$_2$,
OC$_1$-C$_3$ alkyl,
OCOCH$_3$,
OH,
SC$_1$-C$_3$ alkyl,
SOC$_1$-C$_3$ alkyl,
SO$_2$C$_1$-C$_3$ alkyl,
SO$_2$NH$_2$,
SO$_2$NHC$_1$-C$_3$ alkyl,
SO$_2$N(C$_1$-C$_3$ alkyl)$_2$, and
SO$_3$H;

wherein A is selected from the group consisting of N and C;

wherein R$_1$ is an atom of hydrogen or R$_1$ is a C$_1$ to C$_4$ saturated, unsaturated, acyclic, cyclic or mixed hydrocarbyl or modified hydrocarbyl group and wherein, in the modified hydrocarbyl group,
  1 to 2 atoms of carbon may be replaced by 1 to 2 of the same or different heteroatoms selected from the group consisting of N, O, S, Cl, Br and I, and
  1 to 3 atoms of hydrogen may be replaced by 1 to 3 atoms of fluorine;

wherein R$_2$ is a C$_2$ to C$_{13}$ saturated, unsaturated, acyclic, cyclic or mixed hydrocarbyl or modified hydrocarbyl group and wherein, in the modified hydrocarbyl group,
  1 to 4 atoms of carbon may be replaced by 1 to 4 of the same or different heteroatoms selected from the group consisting of N, O, S, Cl, Br and I, and 1 to 5 atoms of hydrogen may be replaced by 1 to 5 atoms of fluorine;

wherein R$_1$ and R$_2$ are different unless fused as a single moiety;

wherein R$_3$ is selected from the group consisting of H and C$_1$-C$_3$ alkyl; and p1 wherein R$_4$ is selected from the group consisting of H and CH$_3$;

with the proviso that, when X$_3$, X$_5$, R$_3$ and R$_4$ are atoms of hydrogen,
  and when X$_4$ is CN or NO$_2$, that R$_1$ and R$_2$ are not CN or OCH$_3$;
  and when X$_4$ is H, CF$_3$, CHO, Cl, CN, COCH$_3$, F or NO$_2$, that R$_1$ is not NO$_2$, SOCH$_3$ or SOC$_2$H$_5$, and that R$_2$ is not NO$_2$, SOR, SO$_2$R, SO$_2$NHR or SO$_2$N(R)$_2$,
  R being an alkyl, cycloalkyl, or aryl group having up to 10 atoms of carbon, or such a group wherein 1 or 2 carbon atoms are substituted by 1 or 2 atoms of sulfur a or oxygen.

31. A sweetening agent according to claim 30 wherein A is N.

32. A sweetening agent according to claim 30 wherein R$_4$ is H.

33. A sweetening agent according to claim 30 wherein R$_3$ is selected from the group consisting of H and CH$_3$.

34. A sweetening agent according to claim 30 wherein R$_1$ is selected from the group consisting of H and CH$_3$.

35. A sweetening agent according to claim 30 wherein X$_3$ and X$_5$ are selected from the group consisting of
H,
Br,
CF$_3$,
CH$_3$,
Cl and
F.

36. A sweetening agent according to claim 30, wherein X$_4$ is selected from the group consisting of
H,
CN,
COOCH$_3$,
F and
NO$_2$.

37. A sweetening agent according to claim 30, wherein R$_2$ is selected from the group consisting of
Normal alk(en)(yn)yl C$_2$-C$_{13}$,
Branched alk(en)(yn)yl C$_3$-C$_{13}$,
Cycloalk(en)yl C$_3$-C$_{13}$,
Alk(en)yl cycloalk(en)yl C$_4$-C$_{13}$,
Cycloalk(en)yl alk(en)yl C$_4$-C$_{13}$,
Alk(en)yl cycloalk(en)yl alk(en)yl C$_5$-C$_{13}$,
Alk(en)yl bicycloalk(en)yl C$_7$-C$_{13}$,
Fused bicycloalk(en)yl C$_7$-C$_{13}$,
Alk(en)yl fused bicycloalk(en)yl C$_8$-C$_{13}$,
Fused bicycloalk(en)yl alk(en)yl C$_8$-C$_{13}$,
Alkenyl fused bicycloalk(en)yl alk(en)yl C$_9$-C$_{13}$,
Fused tricycloalk(en)yl C$_{10}$-C$_{13}$,
Alk(en)yl fused tricycloalk(en)yl C$_{11}$-C$_{13}$,
Fused tricycloalk(en)yl alk(en)yl C$_{11}$-C$_{13}$ and
Alk(en)yl fused tricycloalk(en)yl alk(en)yl C$_{13}$.

* * * * *